(12) United States Patent
Crowley et al.

(10) Patent No.: US 7,743,928 B2
(45) Date of Patent: Jun. 29, 2010

(54) INTEGRATED APPARATUS AND METHODS FOR TREATING LIQUIDS

(76) Inventors: Timothy Crowley, 16656 S. 37th Way, Phoenix, AZ (US) 85048; Vincent B. Pizziconi, 3435 E. Highline Canal Rd., Phoenix, AZ (US) 85042

( * ) Notice: Subject to any disclaimer, the term of this patent is extended or adjusted under 35 U.S.C. 154(b) by 0 days.

(21) Appl. No.: 10/658,447

(22) Filed: Sep. 8, 2003

(65) Prior Publication Data
US 2004/0129678 A1 Jul. 8, 2004

Related U.S. Application Data

(60) Provisional application No. 60/408,677, filed on Sep. 7, 2002.

(51) Int. Cl.
*B01D 35/00* (2006.01)
*G01N 33/48* (2006.01)
*B01D 61/00* (2006.01)

(52) U.S. Cl. .................... 210/433.1; 210/644; 210/767; 210/321.6; 422/101; 422/50; 422/68.1

(58) Field of Classification Search ............... 210/644, 210/645, 656, 198.2, 199, 203; 422/101, 422/102, 55, 58, 73, 82.05, 50, 68.1
See application file for complete search history.

(56) References Cited

U.S. PATENT DOCUMENTS

| | | | |
|---|---|---|---|
| 4,212,742 A | | 7/1980 | Solomon et al. |
| 4,735,722 A | * | 4/1988 | Krepak .................. 210/500.23 |
| 4,753,776 A | | 6/1988 | Hillman et al. |
| 4,797,211 A | | 1/1989 | Ehrfeld et al. |
| 5,204,525 A | * | 4/1993 | Hillman et al. .......... 250/252.1 |
| 5,587,128 A | * | 12/1996 | Wilding et al. ................ 422/50 |
| 5,635,358 A | | 6/1997 | Wilding et al. |
| 5,726,026 A | | 3/1998 | Wilding et al. |
| 5,922,210 A | | 7/1999 | Brody et al. |
| 6,090,251 A | * | 7/2000 | Sundberg et al. ............ 204/453 |

(Continued)

OTHER PUBLICATIONS

Brody et al., "A Planar Microfabricated Fluid Filter," U of Washington Technology Center, 54, 704-708, (1996).

(Continued)

*Primary Examiner*—Krishnan S Menon

(57) ABSTRACT

A passive self energized, liquid device operates entirely on capillary action. A microfilter fractionates nanoliter volumes of suspension such as whole blood into suspended particles or cells and liquid fractions. Blood, for example, is fractionated with minimal cell lysis, and the filtrate (plasma) flux is dependent upon design parameters similar to factors controlling blood filtration in microporous membranes, i.e. active filter area, fluid velocity and microfilter geometry. Weir-style filters communicate with a blood flow channel to separate plasma from blood moving by capillary action. An expanded downstream channel with multiple parallel capillary blood flow path provides continuing movement of blood past the filters. Lysing is controlled by the size of the filter pores and the duration of adherence of the red blood cells to the pores. The controlled lysis or prevention of lysis of red blood cells is accomplished by manipulating the significant capillary forces generated in the filters. Filtration, cell lysis and microchannel blood flow models are integrated into an overall microfilter design useful for fabricating microfilter devices for lab-on-a-chip clinical applications where they can be coupled with on-chip electrical and electro-optical devices.

19 Claims, 20 Drawing Sheets

U.S. PATENT DOCUMENTS

| | | | |
|---|---|---|---|
| 6,106,779 | A | 8/2000 | Buechler et al. |
| 6,156,576 | A | 12/2000 | Allbritton et al. |
| 6,387,290 | B1 | 5/2002 | Brody et al. |
| 6,391,541 | B1 | 5/2002 | Petersen et al. |
| 6,448,047 | B2 | 9/2002 | Dattagupta et al. |
| 6,455,287 | B1 | 9/2002 | Jem |
| 6,488,896 | B2 | 12/2002 | Weigl et al. |
| 6,534,295 | B2 | 3/2003 | Tai et al. |
| 6,544,734 | B1 | 4/2003 | Briscoe et al. |
| 2004/0248167 | A1* | 12/2004 | Quake et al. .................... 435/6 |

OTHER PUBLICATIONS

Moorthy et al., "InSitu Fabricated Porous Filters for Microsystems," Lab Chip, 3, 62-66, (2003).

Zydney, et al., "Continuous Flow Membrane Plasmapheresis: Theoretical . . . ," Transactions of the American Society for Aritificial Internal Organs 28, 408-412 (1982).

Lichtenberg et al., "Sample Pretreatment on Microfabricated Devices," Talanta 56, 233-266 (2002).

Rand, R.P., "Mechanical Properties of the Red Cell Membrane," Biophysical Journal 4, 303-316 (1964).

Sonksen et al., "Home Monitoring of Blood-Glucose," The Lancet 729-732 (Apr. 8, 1978).

Dintenfass, L., "Clinical Applications of Blood Viscosity Factors and Functions," Biorheology 15 (5-6) 486, 1978.

Crowley et al., "Design of a Passive BioSeparation Microfluidic Device," JALA vol. 8 No. 2 78-80 (Apr. 2003).

* cited by examiner

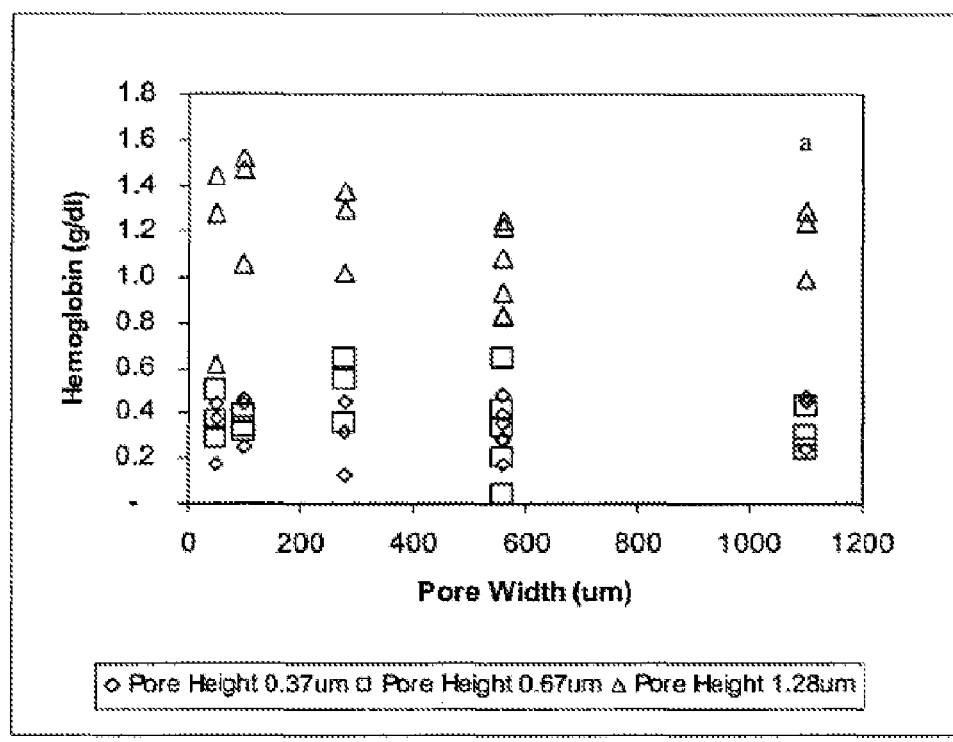
Fig. 16a
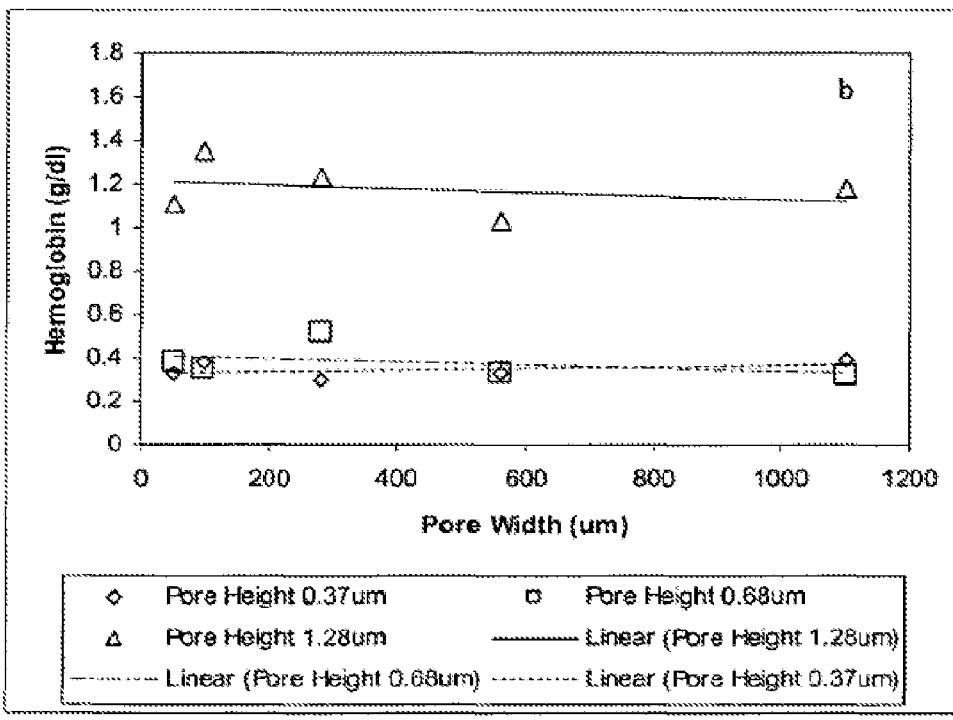
Fig. 16b
Fig. 16

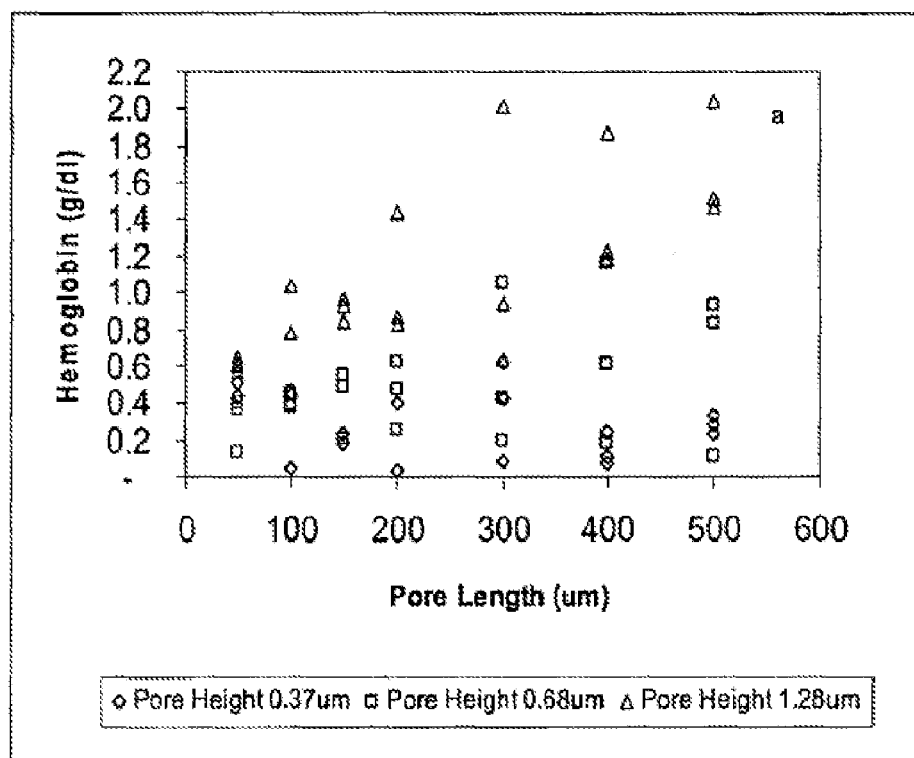
Fig. 17a
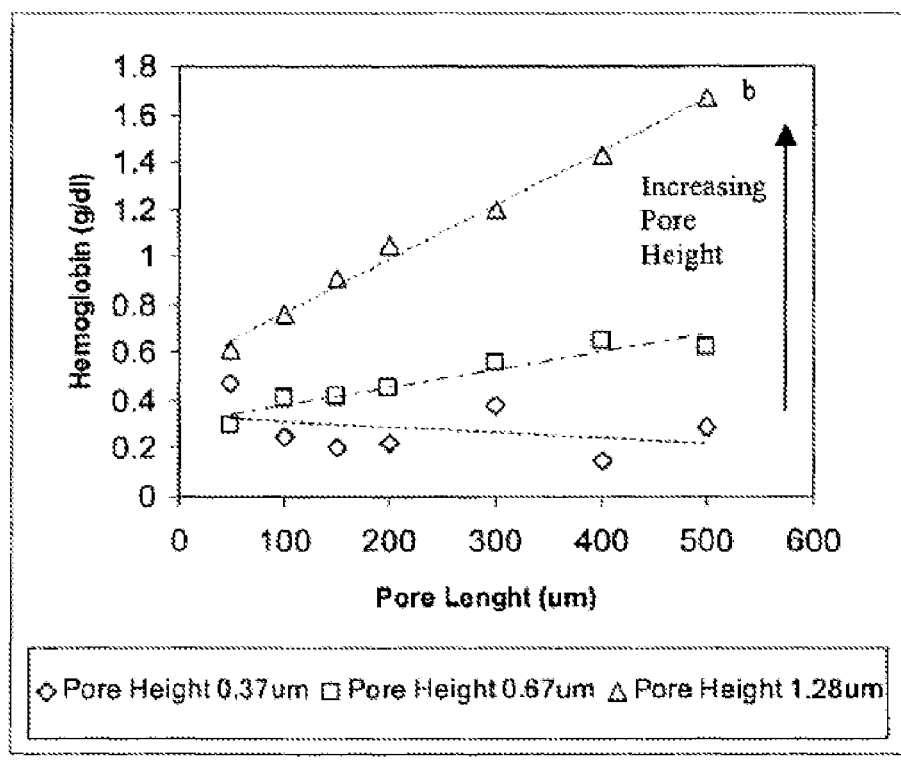
Fig. 17b
Fig. 17

X-Section: Interaction of red cell with filter. Portion outside of filter is spherical.

Top Down View: Portion of the red cell penetrating the filter has a disk shape.

INTEGRATED APPARATUS AND METHODS FOR TREATING LIQUIDS

CROSS REFERENCE TO RELATED APPLICATIONS

This application claims priority from the provisional patent application Ser. No. 60/408,677 filed Sep. 7, 2002 in the name of Vincent B. Pizziconi and Timothy Crowley entitled "Self-Energizing, Scalable and Integrative Hybrid Informatic Method and Apparatus to Manipulate, Process, Diagnose and Treat Complex Fluids" incorporated herein by reference.

STATEMENT OF GOVERNMENT FUNDING

Financial assistance for this project was provided by the U.S. Government through the National Science Foundation under Contract/Grant Number DB1 9602258. Therefore the United States Government may own certain rights to this invention.

FIELD OF THE INVENTION

This invention relates to microdevices and methods for treating, analyzing complex liquids and more particularly to devices of this kind formed on and integrated with semiconductor device supporting substrates.

BACKGROUND

Introduction

The potential of miniature analytical systems in medicine and biotechnology is significant and far-reaching. So called "micro total analysis systems" (μTAS) have the potential to accelerate research in drug discovery, genomics, and proteomics by enabling very high throughput screening of complex samples. They have the potential as well to provide patient "point-of care" capability, and to permit massively parallel bioanalytical chemistry strategies. Although much progress has been made in developing the diagnostics capability of μTAS, to date, little has been done in the way of engineering design and development strategies to allow integrated or modular "on-chip" sample manipulation, preparation and pretreatment for complex biological fluids, such as blood and the like.

Many of the μTAS proposed to date are based upon microfluidic transport of the sample. Microfluidics can be viewed as the physical, chemical, and biological analogue to the integrated circuit. It is the manipulation of fluids on the micron and nanoliter scale using micromachined substrates comprised of complex, miniaturized fluid flow channels and control elements (e.g., baffles, protrusions, flow discontinuities, valves, heaters, pumps) to accomplish micro and nanoscale transport functions in an integrated unit operations process format. Miniaturized chemical analysis systems can reduce the need for skilled labor and reagent cost, improve duty cycle time, reduce production of wastes, e.g. environmental toxins, and while potentially providing the ability to leverage unique small-scale transport effects. For health care applications, the ability to perform point-of-use miniaturization of clinical chemistry will improve patient care, minimize the need to access clinical laboratory facilities and skilled labor, and reduce costs. The use of small scale solid state device liquid treatment and analysis platforms may also permit massively parallel bioanalytical chemistry strategies to be performed useful for telemedicine and other bioinformatic applications.

Microfluidic manipulation of fluids can take advantage of physical and energetic material conditions that are not possible on the macroscale. These include high surface area to volume ratios, and rapid transport processes due to small transfer distances. In addition, the length scale can be designed to take advantage of unique flow behaviors of complex fluids.

Micromachining of microfluidic elements offers a degree of dimensional control in both size and geometry that was not previously possible, providing new capabilities to create innovative biomicrodevices. These microfluidic devices can be made massively parallel to accomplish finely controlled, larger volume processes. However, to take full advantage of these systems additional research and development is required to better understand physical and related scale-dependent energetic phenomena that exist at small length scales and to leverage the unique small-scale effects associated with complex fluids interfacing with other materials.

Complex biological fluids such as blood, cell cultures, and other tissue fluids represent an important class of fluids pertinent to miniaturized chemical analysis. These complex fluids typically require sample preparation to fractionate various fluid components that either interfere with chemical analysis, or provide fluid sub-fractions containing desired analytes. For example, a key operation in the analysis of blood chemistry is the separation of plasma from whole blood. Microdevices engineered with integrated, upstream sample preparation permit direct sample delivery, i.e., blood from a finger stick, and eliminate the need for additional preparatory steps. To date this capability has not been developed, and fundamental design and process research in the area of microfluidic sample preparation is needed to support the commercialization of fully integrated lab-on-a-chip devices (Lichtenberg et al., 2002).

The development of miniaturized devices for the clinical analysis of blood and body fluids is an important application of microfluidic technology. Filtration and separation of blood at the macroscale is typically performed with microporous membranes (membrane plasmapheresis) or using centrifugal techniques. U.S. Pat. Nos. 5,922,210 and 6,387,290 to Brody et al. issued on Jul. 13, 1999 and May 14, 2002 and entitled "Tangential Flow Planar Microfabricated Fluid Filter and Method of Using Thereof" and "Tangential Flow Planar Microfabricated Fluid Filter" describe a liquid specimen treating arrangement that moves liquid along a narrow tube by capillary action from an input reservoir to an output reservoir. Filtration at the microscale is proposed with a weir-style filter. These patents are incorporated herein by reference. Moorthy (2003) teaches filtration of dilute suspensions of isotonically swollen blood cells using in situ fabricated microporous membranes. The utility and cost benefits of miniaturized clinical chemistry to improve patient care has already been demonstrated with the point-of-use blood glucose monitoring systems that dramatically improve diabetic glucose control (Sonksen et al., 1978, Walford et al., 1978). Similar benefits are expected with the development of highly integrated lab-on-chip devices with the capability to measure multiple blood analytes from a single drop of blood.

To date, microfluidic research applied specifically towards the needs of clinical chemistry has been limited. This is needed to develop the practical, enabling platforms required to realize these miniaturized clinical devices. These include miniaturized optical detection schemes, nanoliter chemical delivery, microscale mixing, and, in blood work, microfluidic separation of plasma from whole blood.

As for cell lysis, where that, rather than just filtration is desired, lysis of blood for microscale applications has been proposed using chemical lysing agents. Mechanical lysis using externally applied energy (pressure) and through the use of electric fields has been described. No known prior art has proposed the lysis of cells using only capillary action for microscale operations that are thus "passive." As used herein "passive" means operable without the application of an external force or energy as in the case of movement of a liquid solely by capillary action.

In the embodiment of the present invention, the level of stress applied to cells can be very precisely controlled using passive surface energy and precise geometrical structures. Various levels of lysis may be achieved using this technique. With the present invention, using specific filter parameters, geometry, etc. is believed possible to selectively lyse specific cell types while other cells are not lysed, e.g. white blood cells vs. red cells.

Characterization of rheological properties of complex fluids is traditionally done with sophisticated rheological equipment, e.g. cone/plate viscometer or rheometer equipment. The devices are typically bench top instruments requiring external energy, sophisticated mechanisms and equipment to measure the rheological properties of complex fluids and volumes on the order of milliliters. Again passive microscale devices suitable for lab-on-a-chip use are desirable according to embodiments of the present invention.

BRIEF SUMMARY

A passive, self-energizing small (micro-nano) scale liquid treatment and analytic microtool according to this invention uses capillary action to move and manipulate a liquid specimen. The specimen may be a single sessile drop of the liquid specimen being manipulated and tested.

In a preferred embodiment, a flow channel in which the liquid specimen moves by capillary action from an input reservoir leads to an expanded channel. There, parallel liquid paths connected to the flow channel sustain the presence of the motivating force and thus duration of capillary action moving the liquid in the flow channel. This extends the device operating time. A comparable in length flow channel without the expansions described here is estimated to be able to operate for about 15 seconds, whereas with this expanded channel here described operation times up to two minutes are possible. Filters opening from the flow channel direct liquid of desired specimen subfractions filtered from a specimen to a collection region. Again capillary action is the motivating force. The arrangement is particularly useful in the fractionation of a complex fluid suspension such as blood, where suspended matter such as macromolecules and formed elements (e.g. red and other blood cells) are moved along the liquid flow channel and while a desired subfraction of filtrate such as plasma exits via the filter constructs into the collection region. Plasma production is in the nanoliter range compared to the picoliter of the prior art "straight channel" device.

In one exemplary embodiment the liquid specimen or filtrate from the specimen is moved along a liquid flow channel by capillary action and in accordance with the invention to locations where portions of the liquid are tested or examined. Liquid testing apparatus is provided to test the liquid in each of the wells. Optical, chemical, biological and electrical testing may be carried out on the liquid with or without reagents.

Broadly, in accordance with one aspect of the invention the method of liquid treatment and analysis comprises devising a set of heuristic design rules from the behavior of nanoliters of a particular liquid, fabricating as a part of a liquid treatment and analyzing instrument a liquid contacting device based on one or more of the heuristic rules and providing a means of determination of a characteristic of the liquid based on the liquid's behavior in contact with the liquid contacting device. Process models and design conditions have been established that permit the a priori design of microfilter device to meet specific design constraints.

In the case in which the liquid comprises a suspension of particles, such as colloids and cells, devising heuristic rules includes determining parameters of the liquid contact device that affect lysis of the cells, and the fabricating of the liquid contacting device includes implementing selected values of the parameters to provide the desired presence or absence of lysis of the cells. A particular preferred and exemplary embodiment of this method is applied to blood fractionation in which blood cells, such as red blood cells, suspended in plasma are the cells and the parameters include cell stress and cell stress duration.

An instrument made pursuant to the heuristic rules in accordance with the invention in one embodiment includes a liquid input opening, a first passage leading from the liquid input opening and operative to move liquid therealong by capillary action, a filter communicating between the first passage and a filtrate collection location to which the filtrate flows, again by capillary action, and an expanded liquid flow path for passing the liquid from the first liquid passage to a further location. The expanded liquid flow path preferably comprises a plurality of liquid flow paths connected to receive liquid flow in parallel from the first passage and sized to move the liquid therein by capillary action. In this flow network arrangement, the multiple parallel capillary action paths sustain the movement from the input location through the first passage in communication with the filter for a longer period of filtration and collection of a higher quantity of filtrate than if only the single, first passage were employed. As apparent here and from exemplary embodiments that follow the parallel nature of the flow paths of the expanded channel and of the flow therein that is important here is not that the flow paths are parallel in the geometric sense, but rather that they connect to the primary flow path from the liquid input location to cause concurrent capillary action flow, which is more like "parallel" current flow in the electrical circuit sense.

In another exemplary embodiment of the invention, controlled lysis of cells in a suspension such as red blood cells in liquid whole blood is accomplished. Again, filter openings or pores communicate through the sides of a liquid flow channel along which the suspension moves by capillary action. The size of the pores and the length of a passage from the pore that draws liquid to a collection site are chosen to provide controlled levels of cell stress and duration and thus control the level or prevention of lysis of cells that adhere to and are deformed by the filter opening. The factors that affect lysing are stress on the cell and the duration of such stress. In the case of fractionation of a suspension such as whole blood, where only liquid such as plasma is desired as the filtrate, then the filtrate flow channel away from the filter to the filtrate collection site is made sufficiently short as to shorten the time of residence of a cell at the filter pore particularly during the initial wetting period when capillary pressure across the filter pore or pores is greatest. On the other hand, if a greater or lesser degree of lysis is desired, then, a longer channel is used.

An exemplary instrument for measuring capillary pressure is a part of this invention. An encapsulation of entrapped gas, air for example, is provided proximate a flow of liquid by capillary action. A tube from the path of liquid flow to the gas develops a column of the liquid that acts against the gas to an extent that is indicative of the capillary pressure present. The location of the meniscus of the liquid column is detected as an indicator of the capillary pressure. A pair of these pressure measuring arrangements spaced apart in the direction of liquid flow can serve as a flow meter.

Where the liquid under examination is clear (i.e. transparent), a preferred method of illuminating the liquid allows its observation. A substrate is provided on which an at least partially light transmitting layer is present and forms with the substrate an interface. The liquid specimen is supported on the surface of the at least partially light transmitting layer. Because of differences in indices of refraction, the critical angle of reflection at the surface of the at least partially light transmitting layer changes. This permits visible interference between light reflected from and light refracted through the layer to be altered or eliminated so that the presence of absence of a liquid on surface of the layer is more readily observed. A specific exemplary embodiment of the method and device employs a silicon substrate on which a silicon dioxide layer has been grown to serve as the at least partially light transmitting layer of the device.

In particular exemplary embodiments of the invention a plurality of specimen treating devices of the kind described above have been integrated into a single semiconductor chip. As many as eight filtration units have been formed on the chip. Preferably the units share at least one vent line connecting filtrate collection regions and outputs of the flow channels to at least one opening to atmosphere. The expanded flow channel with parallel capillary flow paths can be prepared such that the parallel capillary flow paths are formed in a serpentine pattern so as to be fit, with other such parallel capillary flow paths, on the single semiconductor chip. Additional features carried by the chip include passive hematocrit measuring arrangements for moving blood by capillary action through a serpentine path. The distance the whole blood moves is a measure of % hematocrit.

A filtration and separation method is provided that is adaptable to microscale technologies. Neither membrane plasmapheresis nor centrifugation is readily adaptable to lab-on-a-chip type applications. The techniques required to fabricate membrane type technology in microchannels is not well established. Additionally, the use of centrifugation at the microscale is problematic for the following reasons: 1) g-forces achieved in centrifugation are related to the angular velocity and the radius of rotation. The radius of rotation in microdevices is small and very high rotation rates, >15000 rpms, are required to achieve the g-forces required to separate biological fluids such as blood. 2) rotation requires additional mechanical equipment and a power supply. The passive devices of this invention do not require any external energy or equipment. The performance of the proposed device as measured on a filter flux basis is significantly higher, 3-5× higher than membrane plasmapheresis.

Typically the liquid volumes being treated are of the nanoliter size. Ordinarily, a single drop of the liquid suffices for the purposes of the invention. In one exemplary embodiment the liquid flow channel that draws the liquid past the weir-like filters is of a cross-sectional dimension less than 10 μm and greater than 0.1 μm. Preferably the dimension is about 0.5 μm.

The devices can be used to measure the rheological properties of complex fluids without external energy sources. They do not require sophisticated electronic and mechanical equipment. Measurement is made simply by measuring the distance the fluid traveled in specifically designed microchannels. These devices are suitable for having the measurement and readout performed by an optical assessment of the fluid position using only, for example, a CCD camera. Using a micromachining device can achieve very finely controlled geometrical and flow conditions that are not achievable with typical macroscale devices.

An exemplary embodiment of the method of fabricating the liquid specimen handling devices of the invention uses techniques similar to those used in the fabrication of integrated circuits. A photoresist is deposited on a semiconductor substrate. A mask defining the liquid flow provisions of the device is brought into place and the photoresist is exposed to UV light through the mask. The photoresist is removed in locations that have been exposed to the UV light. A semiconductor is etched in areas revealed by the removal of the photoresist to form the liquid flow provisions and other features of the device. A closure layer, typically a glass lid, is secured to the semiconductor substrate over the etched channels and other device features. Where weir-like filters are to be prepared, either before or after forming the liquid flow channels, just one further mask defining filter pores is brought into alignment with the semiconductor separate and aside from the foregoing steps and the procedure of exposing a photoresist on the surface of the semiconductor to UV light is used in relation to just the areas that are to be the pores of the filter. The exposed photoresist areas are removed and the pores are etched to a depth that is less than that to which an adjacent flow channel is etched.

The above and further features and advantages of the invention will be better understood with reference to the following detailed description of preferred embodiments taken in consideration with the accompanying drawings. The illustrations in the various Figures of the drawings are for explanatory purposes, and unless otherwise noted, are diagrammatic and not to scale.

BRIEF DESCRIPTION OF THE DRAWINGS

FIGS. 16a and b are plots of hemoglobin concentration and plasma filtrate vs. filter pore width showing, in (a), individual results, and in (b), average of three tests per point with filter pores 200, urn long;

FIGS. 17a and b plots hemoglobin concentration and plasma filtrate vs. filter pore length at three pore heights showing individual results: (a) an average of three tests per point, and (b) with filter pores 500, urn wide;

DETAILED DESCRIPTION

Microfilter

Figure 1:
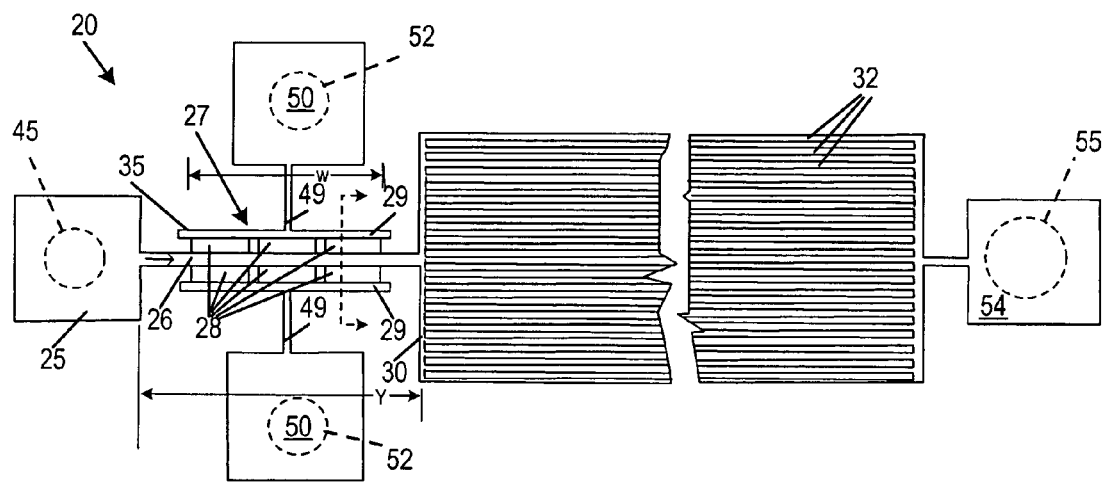
FIG. 1 is a diagrammatic illustration of a microfilter formed on silicon in a manner similar to semiconductor fabrication.
Figure 2:
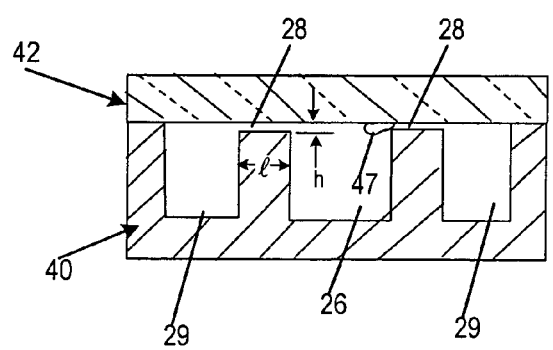
FIG. 2 is a diagrammatic cross section along the lines [2-2] 28 of FIG. 1 and shows a pair of weir-like filters opening from a main fluid channel to two filtrate receiving side channels.

As illustrated in FIGS. 1 and 2, a microfiltering system 20 is fabricated in silicon and glass. This is done using methods similar to those used in integrated circuit fabrication as described below. The microfilter 20 has an input reservoir 25, a narrow filtration channel 26 containing a pair of transverse flow microfilters 27, a pair of plasma outlet channels 29 to collect filtrate. A downstream expanded channel 30 connects in series with the filtration channel 26. In one exemplary embodiment, the expanded channel 30 of the device contains an array of parallel, ~45 μm wide, and 15 mm long flow channels 32, as shown in FIG. 1.

The microfilter 27 is a weir type filter fabricated as a series of rectangular openings 28, the 'filter pores', located on both sides of the 100 μm wide filtration channel 26. In one preferred exemplary embodiment, used for the fractionation of nanoliter amounts of whole blood, the dimensions of each filter pore was a width 'w' 200 μm wide, a height 'h'<1 μm high, and a length 'l' ~30 μm long. The ~30 μm length represents the length 'l' between the blood flow channel 26 and a plasma outlet channel 29 as illustrated in FIG. 2. The total 200 μm width 'w' of the active microfilter section is approximately 75% of the filtration channel length 'y'. Also, the pores 28 of the filter were centered over the length of the filtration channel 26.

As shown in FIG. 2 the features of the microfilter are formed in a Si substrate 40 and are covered over by a glass lid 42. The broken line circle in FIG. 1 represents a hole 45 bored into the glass lid 42 above the input reservoir 25 for the introduction of a drop of liquid to be separated or in the case of blood "fractionated." In the case of whole blood, red blood cells 47 are greater in cross-sectional dimension than the height of the pores 28. Plasma, the filtrate, is delivered to plasma outlet channels 29. From there the filtrate is drawn through a pair of narrow channels 49 by capillary action to a pair of reservoirs or collection regions 50. As indicated by the broken line circles at the reservoirs 50, a pair of further holes 52 vent the reservoirs to atmosphere to permit filtrate flow to the reservoirs.

Capillary action in the filtration channel 26 initiates the flow of specimen liquid therein and capillary action in the flow channels 32 of the expanded channel 30 continues to draw the specimen liquid into and along the filtration channel 26. In the case of blood the red cell rich suspension in the parallel channels 32 is delivered toward output reservoir 54 that is also vented to atmosphere by a hole 55 in the glass lid or closure 42.

It was determined that plasma flux across the filter is substantially independent of the % hematocrit of the specimen. This is an unexpected and beneficial result for clinical use of such microfilter device, making their performance very much independent of % hematocrit variances among individuals or within an individual.

In the microfilters as described, generally, the red cell rich (high % hematocrit) flow in the expanded channel would not reach the end of the parallel capillary flow paths. This arose either by blocking of the vent line or by stoppage of the viscous sludge-like blood flow high in red blood cell content by virtue of the filtering off cell free filtrate subfractions, such as plasma.

Two approaches help to sustain the movement of liquid in the flow channel. First, increase the available surface energy to sustain capillary action by extending the effective length cross-section, and aspect ratio of the blood flow path and thus surface area in the expanded channel. This can be achieved by making the extended flow channel longer, increasing the surface roughness of the flow channel, changing the cross-sectional area, length to height to width ratios, or extending the 2-D planar flow channel into higher dimensions, i.e. 3-dimensions (x,y,z). These conditions will allow the desired level of shear rate for a desired amount of extraction of filtrate subfraction to be obtained. For example, just narrowing the expanded channel will increase the velocity of flow there to enhance shear rate. Second, attention to the number of pores of the filters and their size and distribution so as to control the amount of plasma transferred out of the flow will reduce the tendency of premature blood flowing in the expanded channel. Limiting plasma reduction to 10% or less is desirable to these ends.

Single Chip Multi-Filter

Two different multi-microfilter device designs are referred to as 'Weir 10' and 'Weir 11'. The design of the flow channel network and microfilter barrier geometry is identical between the two designs. However, the total width and resultant surface area of the expanded channel, and the layout of the plasma outlet channels are slightly different. The total width of the expanded channel area (i.e. the total number of individual parallel channels) was specified at a magnitude proportional to the filtration channel length to achieve an acceptable level of shear rate in the expanded channel. Table 1 provides key design features for both designs and Table 2 summarizes the Weir 10 and Weir 11 design differences.

ing the parallel capillary flow paths, while the Weir 10 devices utilizes the long narrow channel 86, 87 and 88.

Passive microfilter devices like Weir 10 (FIG. 3) and Weir 11 (not shown) operate successfully to isolate up to ~50 nl of plasma from whole blood without significant levels of hemolysis. These devices effectively separate nanoliter volumes of plasma utilizing only capillary action in a design platform that supports integrated sample preparation for lab-on-a-chip devices. Additionally, the microchannel layout with the expanded channel extends the passive operation time of these devices by several fold, i.e. a few seconds to several minutes.

TABLE 1

Key microfilter design features.

| Target Shear Rate $sec^{-1}$ | Main Channel Length (mm) | Weir 10 Design Number of Individual Channels in Expanded Area | Weir 11 Design Number of Individual Channels in Expanded Area | Filter Length (mm) | Number of Filter Pores |
|---|---|---|---|---|---|
| 5000 | 2 | 100 | 50 | 1.4 | 12 |
| 2500 | 4 | 50 | 25 | 2.8 | 24 |
| 1100 | 15 | 14 | 7 | 11.3 | 94 |

TABLE 2

Key design differences between Weir 10 and Weir 11 microfilter designs.

| Design Feature | Weir 10 | Weir 11 |
|---|---|---|
| Total Width of Expanded Channel | 2 times larger than Weir 11 | ½ size of Weir 10 |
| Expanded Channel Target Shear Rate ($s^{-1}$) | 100 | 200 |
| Device Layout on Wafer | Three devices integrated into a common test cell. | Devices laid out individually across wafer |
| Venting | Integrated vent line shared by three devices | Individual venting for each device |
| Plasma Outlet channels | Long narrow channels ~60 um wide | Large rectangular collection areas 3 mm wide |

Figure 3:
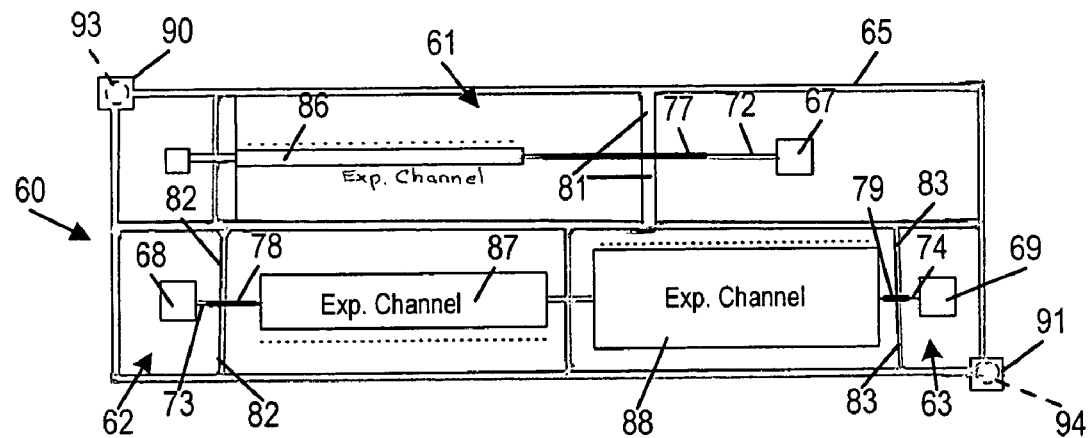
FIG. 3 is a diagrammatic illustration of three microfilters sharing flow-enabling vent lines on a single silicon chip.
Figure 6A:
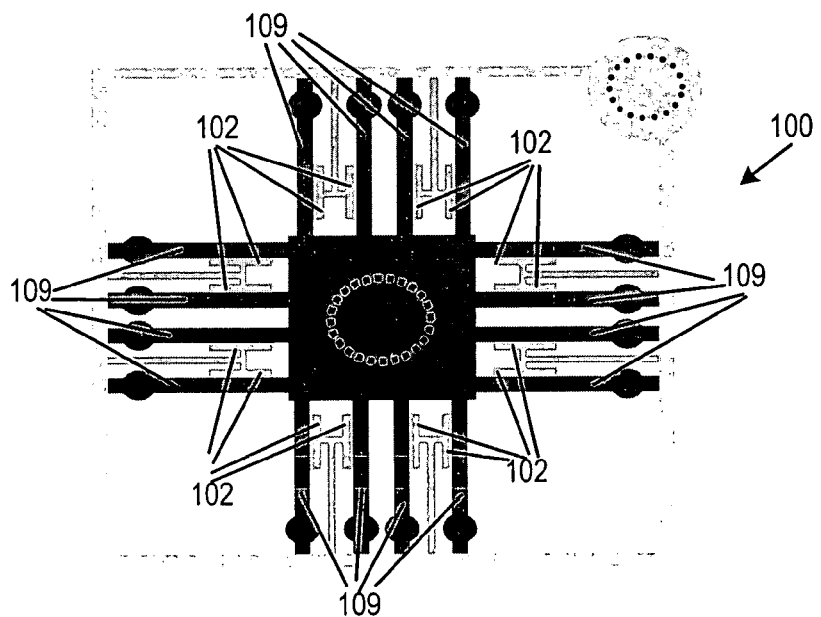
FIGS. 6a-6c are diagrammatic illustrations of a multi-channel analysis chip with electro-optical test provisions.
Figure 6B:
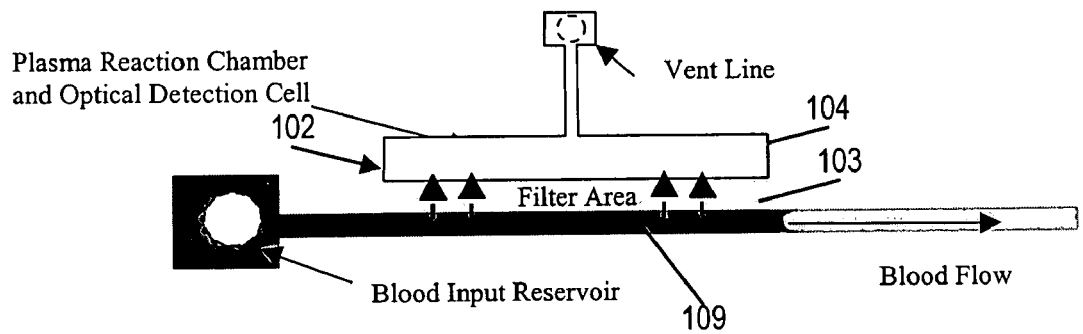
Figure 6C:
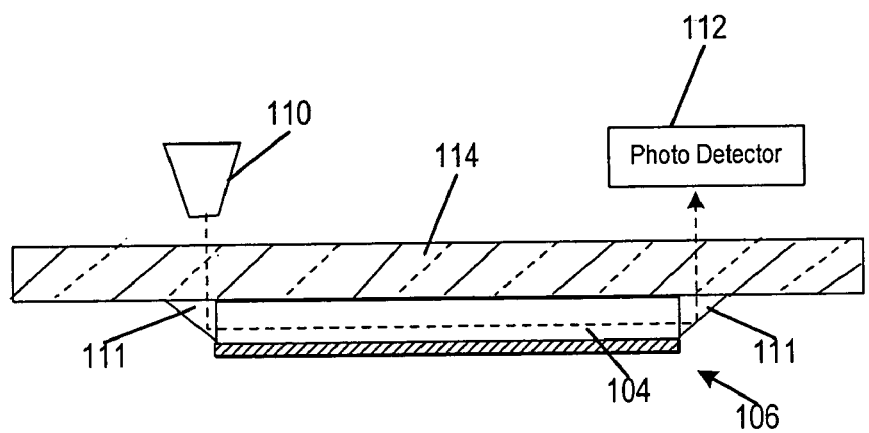

Shown in FIG. 3 is the Weir 10 multiple filter device 60 layout integrating three microfilters 61, 62 and 63 into a single test cell sharing a common channel 65 that allows the displaced air to vent during wetting. Three input reservoirs 67, 68 and 69 feed three filter flow channels 72, 73 and 74. Three weir-style filters 77, 78 and 79 divert liquid filtrate to three sets of filtrate output flow channels 81, 82 and 83. Three expanded channels 86, 87 and 88 of differing geometry contain parallel capillary flow paths (not separately shown). At reservoirs 90 and 91, connected with the common vent channel 65, vent holes 93 and 94 are drilled in a glass lid that overlies the features etched in Si to form the multi-filter device 60. The Weir 11 microfilter devices utilizes individual vent holes instead of the integrated vent line 65 used in the Weir 10 design. Also, the Weir 11 plasma outlet channels were designed as large, wide rectangular open areas, contain- Multi-Channel Analysis Chip As shown in FIGS. 6a-c, a generalized bioanalytical microdevice 100 illustrates the potential impact of microfluidic research on clinical chemistry. This device is a "micro sequential multi-channel analysis chip" (uSMAC) and has the capability to perform, at 16 locations 102, 16 different blood tests from a single drop of blood. This disposable test cartridge 100 contains microfilters, shown diagrammatically in FIG. 6b at 103 for the separation of plasma, plasma collection chambers 104 for chemical analysis, and optical detection cells 106, FIG. 6c for quantification of the analytes. Analysis is initiated by placing a drop of blood from a finger stick on the inlet reservoir 107. As blood flows through the device via capillary action, plasma is separated by the microfilters located on each of the sixteen analysis channels 109. Each plasma outlet chamber 104 contains analysis reagents FIG. 6c and forms a horizontal optical detection cell with a 2 mm long optical path length, requiring only nanoliter volumes of plasma. The test cartridge is evaluated using a handheld device, similar to commercial glucose test systems, containing the optical and electrical systems required to quantify the test results. These may include a laser 110 and a photodetector 112, for example, as shown, viewing the analyte through the glass cover 114 of the device using mirrored sidewalls 111 of the optical detection cell. With large-scale integration of microfluidic and microelectronic devices, it becomes possible to integrate all these functions into a stand-alone test cartridge. As nanotechnology progresses, it is believed it will be possible to develop a fully implantable, uTAS system. In any case, the realization of such a device has broad reaching implications for patient care and the availability of sophisticated clinical analysis to the general populace.

Figure 13A:
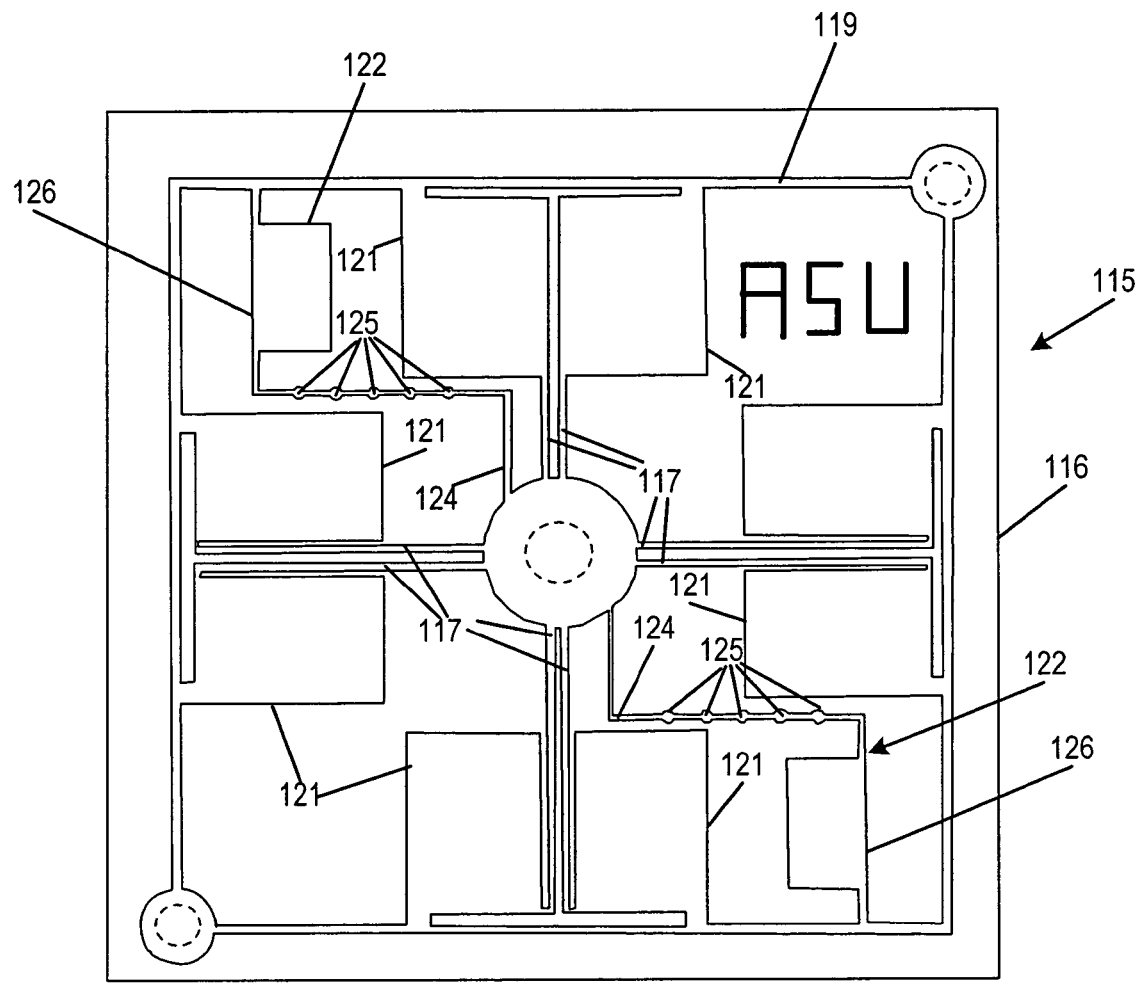
FIG. 13a is a top plan view of a silicon-based integrated fluid device incorporating eight filters and a pair of hematocrit meters on a single silicon chip.
Figure 13B:
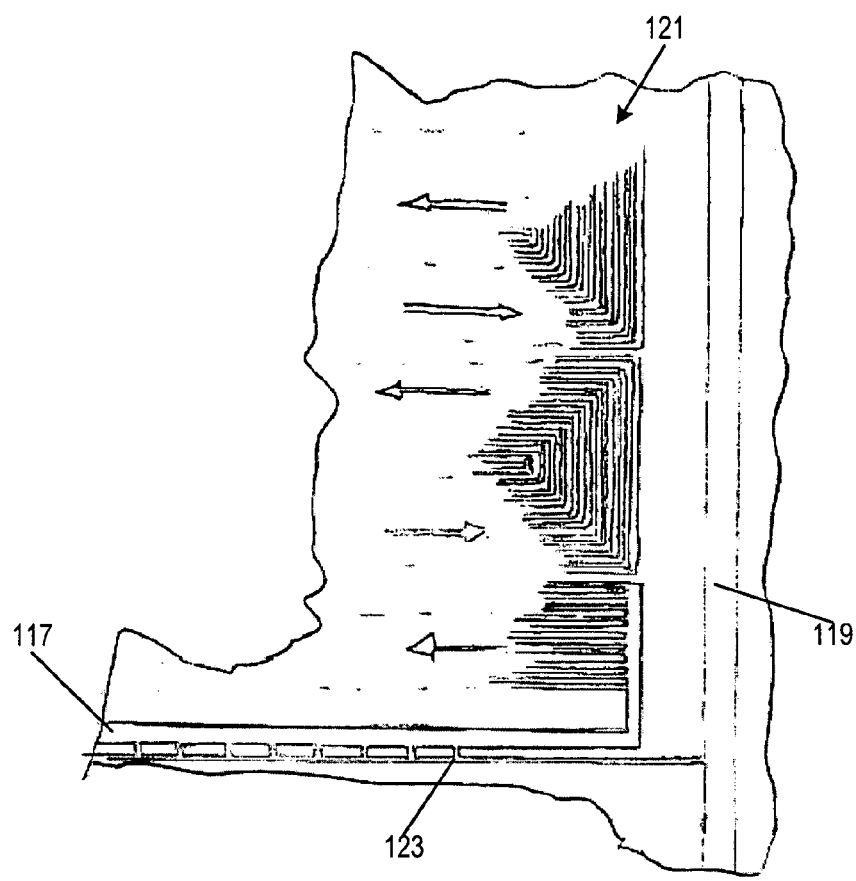
FIG. 13b is an enlarged fragmentary plan view of the device of FIG. 13a and showing a series of parallel, serpentine capillary flow paths.

Using the design rules and the operation model described herein, a multi-channel microfilter device 115 was designed and fabricated as shown in FIGS. 13a and 13b. This device has the capability to isolate blood plasma in eight separate microchannels 123 (FIG. 13b). The device includes, on a single Si chip 116, eight integrated expanded channel microfilter devices connected to a common input reservoir 118 and utilizing a common air vent line 119. It also uses ~8 mm long filtration channels 117 with 10-channel expanded channel sections 121 utilizing a serpentine flow channel layout best illustrated in FIG. 13b.

Also included in the multi-filter construction of FIG. 13A are two integral hematocrit test devices or gauges 122. In these a single capillary flow channel 124 leads from the common input port 118, through a series of flow retarding chambers 125 to a single serpentine section 126 of the channel 124. The channel 124 is vented, at the far end of its serpentine section by the common vent line 119.

The distance along the single channel 124 that the whole blood from the specimen travels by capillary action is a function of the % hematocrit of the specimen introduced to the reservoir 118.

Preliminary testing of the device was performed using whole bovine blood. Blood was observed to flow uniformly through all eight filtration and serpentine structures. Also, plasma was successfully isolated in all 8 plasma outlet channels and the µSMAC prototype device demonstrated that blood could be fractionated using a multichannel microfilter design. These preliminary results support the feasibility of developing massively parallel multi-channel blood analysis devices for in vitro clinical chemistry applications, biotechnology, and potentially in vivo applications.

Microfilter Design Heuristics

Based on the tests described below, the following heuristic rules were determined:

The control of hemolysis is a key design specification for lab-on-a-chip applications. The filter pore geometry, i.e. pore height h, was determined to be a key factor. Hemolysis can be minimized in microfilter design through the use of pore heights <0.5 um or some equivalent pore diameter, De.

Filter pore length l was found only to have a secondary effect on hemolysis, and can be limited by minimizing the filter pore length.

The filter pore residence time model of hemolysis, developed in this study, was qualitatively in good agreement with the experimental results, i.e. larger filter pore heights permit greater deformation of the red cell 47 into the filter pore (at 125 in FIG. 4, for example) than smaller filter pores.

Hemolysis is increased with filter pore geometries that increase residence time of the cells in contact with the filter pore whereupon red cells are subjected to the significant capillary pressures present upon initial wetting of the filter for a longer period of time.

Microfilter Cell Lysis Background

Figure 4:
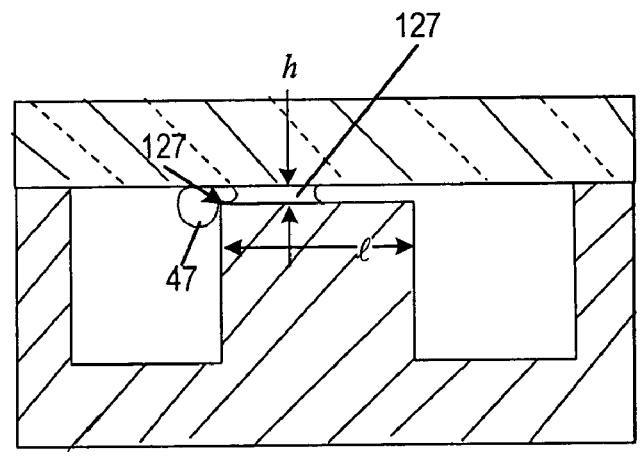
FIG. 4 is a diagrammatic, enlarged cross-sectional view of a single weir-like filter having a red blood cell adhering to its input opening.

Cell lysis, e.g. red blood cell hemolysis, can occur in microfilter devices due to the deformation of red cells into sub-micron sized filter pores, and the membrane stresses generated by the transfilter pressure, as shown in FIG. 4. In capillarity-driven microfilters, the highest transfilter pressure is generated upon initial wetting of the sub-micron filter pore by capillary action when capillary pressure is generated by plasma 127 initially crossing the filter, after which it decreases when fluid reaches the deeper plasma outlet channel where the capillary pressure is reduced. The apparent capillary pressure generated in the filter pore can be substantial, and it is at least an order of magnitude higher than the pressure generated by the outlet channel.

Hemolysis, and cell lysis in general, is a time-dependent function of stress, i.e. hemolysis occurs more quickly at high stress and slowly at low stress. Alternatively, hemolysis can be prevented at high stresses if the exposure time is very short, and at longer exposure times if the stresses are lower. In microfilter devices, the duration and level of stress generated by filter wetting is related to the filter pore dimensions of length, width, and height. Filter length controls the time that the high capillary pressure, generated by filter pore wetting, is present at the filter face, as this parameter determines the length of time for plasma to cross the filter and reach the deeper plasma outlet channel. The filter pore width and height affect the capillary pressure generated across the filter barrier. Also, these parameters can affect the shape of the red cell deformation or the residence time of the cell in the filter. As such, hemolysis experiments were conducted to investigate the effects of pore length, height and width as these parameters control the duration and level of stress applied to red cells.

Hemolysis Test Devices

Methods

Figure 7:
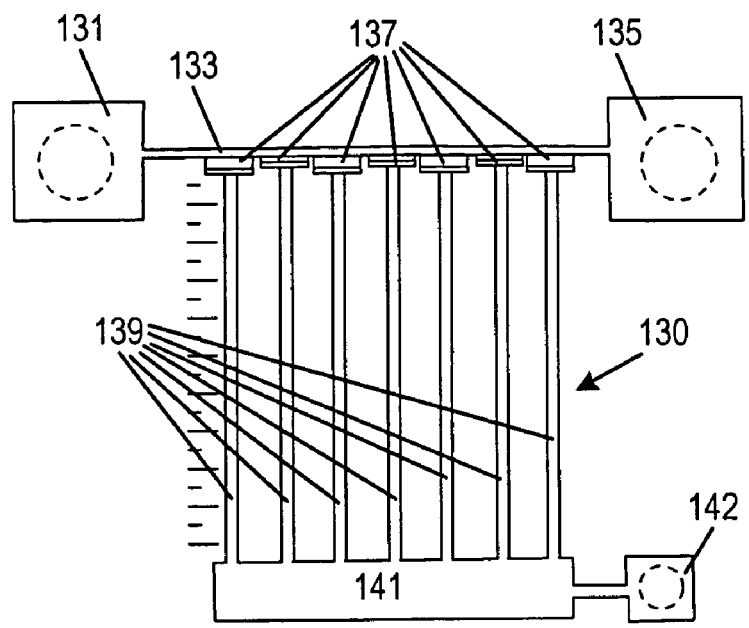
FIG. 7 is a diagrammatic illustration of a series of filters of varying lengths in communication with a blood flow channel.
Figure 9:
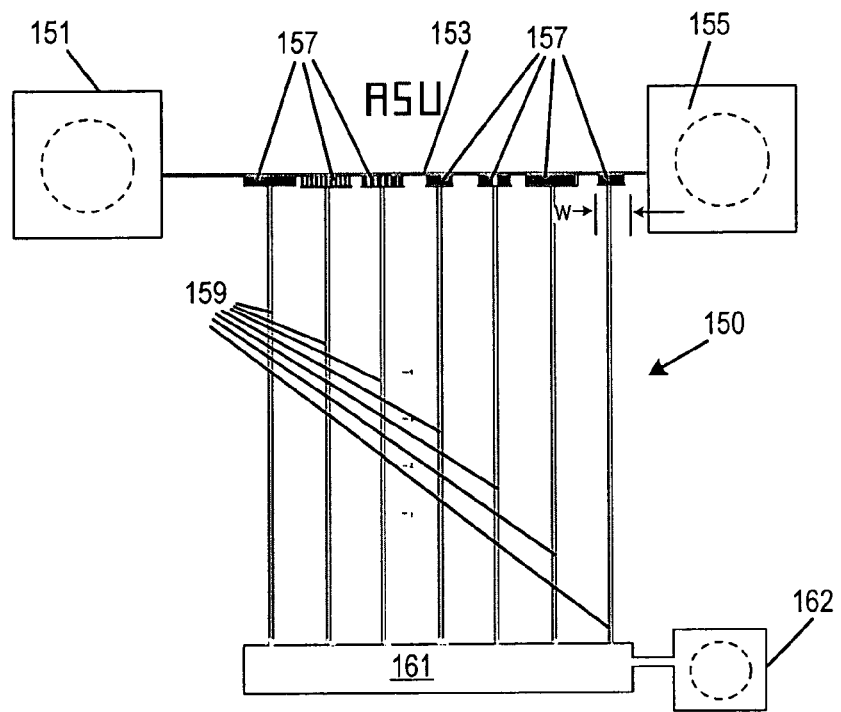
FIG. 9 is a diagrammatic illustration like FIG. 7 of a series of filters of varying lengths in communication with a blood flow channel.

Microfluidic separation devices designed to assess factors controlling hemolysis were fabricated in silicon and glass with the techniques of the present invention. Test structures were developed to characterize the effects of filter geometry on hemolysis. On-chip calorimetric techniques were also developed to assess the level of hemoglobin in the nano-liter volumes of plasma filtrate as a method to quantify hemolysis. Hemolysis test devices varied the pore length, width, and height over the experimental range shown in Table 2. Two basic hemolysis test device designs were utilized, one device 130 was designed to vary the filter lengths l as shown in FIG. 7. The second test device 150 was designed to vary the filter width w as shown in FIG. 9. Both test devices were fabricated at three different pore heights h. The blood flow channels were 100 µm wide, and plasma outlet channels were 60 µm wide.

Figure 8:
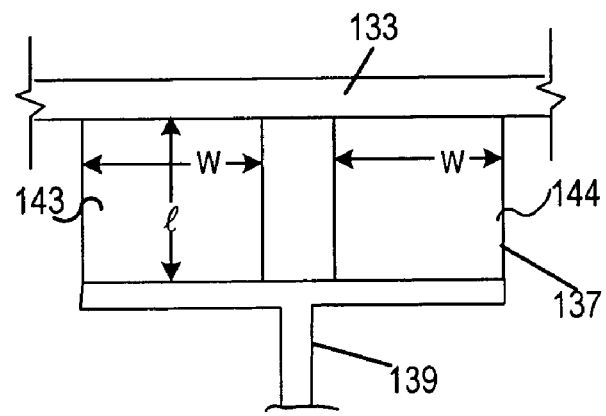
FIG. 8 is an enlarged fragmentary illustration showing one of the filters of FIG. 7.

In FIG. 7a blood plasma is introduced at a reservoir 131 and travels by capillary action through a flow channel 133 to an output reservoir 135. Along the way the blood plasma passes a series of the weir-style filters 137 of varying lengths. Plasma and any lysed cell is carried by capillary action of tubes 139 to a collection region 141. The tubes 39 and the collection region 141 are vented at 142. FIG. 8 is an enlarged illustration of one of the filters 137 in association with the flow channel 133 and the tube 139 therefrom. Two pores 143 and 144 are shown. Each has a length l and a width w.

Similarly, FIG. 7b illustrates a hemolysis test device of variable filter width w. It has an input reservoir 151 from which blood flows along a flow path 153 to an outlet reservoir 155. Filters 157 have varying pore widths w. The core width w is illustrated in FIG. 8. Again tubes 159 carry plasma by capillary action to a collection region 161 vented to atmosphere at 162.

Hemolysis testing was performed at room temperature by applying approximately 10 μl of citrated whole bovine blood to the input reservoir of each test device using a micropipette, after which blood flowed spontaneously through the device via capillary action. After blood ceased, the plasma filtrate produced by each microfilter was digitally photographed at 100× using a Mitutoyo Ultraplan FS110 optical microscope (Aurora, Ill.), and a JVC TK-1280U color video camera (Cypress, Calif.). The concentration of hemoglobin in the plasma filtrate was measured using a colorimetric comparison, between the plasma filtrate and four hemoglobin reference standards, 0, 1.7, 3.3, and 6.7 g/dl, incorporated into each wafer. The colorimetric assessment of hemoglobin standards and the plasma filtrate was based on digital color analysis of the hemoglobin and isolated plasma using the red, green, blue (RGB) color model. The redness of the hemoglobin standards and plasma filtrate was quantified by calculating the average percent red pixel value per equation the following equation for % Red. A correlation between percent and hemoglobin concentration was established using the on-wafer hemoglobin reference standards and utilized to quantify the hemoglobin concentration in isolated plasma.

$$\% \text{ Red} = \frac{\text{Red Pixel Value}}{\text{Red} + \text{Green} + \text{Blue Pixel Values}} \quad (1)$$

Hemoglobin standards were prepared from citrated bovine blood. The isolated red blood cells were washed. Red cells were hemolyzed. The isolated hemoglobin solution was then diluted with DI water to produce three solutions containing 1.7, 3.3, and 6.7 g/dl hemoglobin as determined by absorbance measurements. Water was used as the zero hemoglobin reference. The hemoglobin reference solutions were placed in specific microfluidic channels on each wafer and sealed with epoxy to prevent evaporation.

The volume of plasma fractionated by each filter was calculated using digital analysis of optical micrographs. The area of the outlet channel filled with plasma was first measured, and multiplied by the known channel height to calculate plasma volume. Plasma flux for each filter was then calculated by dividing the plasma volume extracted by the filter area and time of operation.

Hemolysis testing and evaluation was performed on 115 individual microfilter test structures. The volume of plasma and the concentration of hemoglobin in the plasma was quantified for each device and compared to filter parameters of pore height, width, and length. Test devices were fabricated on three silicon wafers, each wafer included five filter length and five filter width test devices (FIGS. 7a-7b). Each wafer was fabricated at one of three pore heights, 0.37, 0.67, or 1.28 urn. The average channel height of the blood flow and plasma outlet channels was 21 urn.

Bovine blood specimen with a hematocrit of 38.5% was used for the hemolysis testing. Results for hematocrit, viscosity, total protein and fibrinogen concentration were consistent with other bovine blood specimens used in this research.

Figure 15:
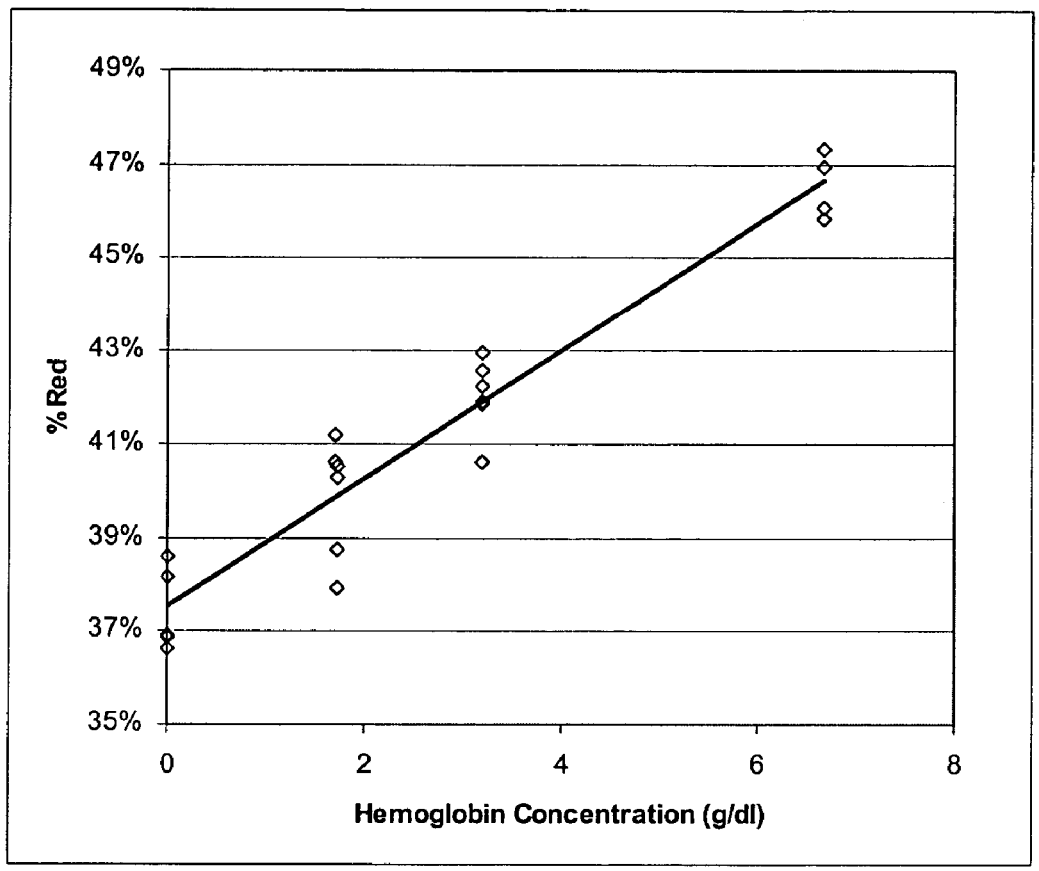
FIG. 15 is a plot of individual percent red pixel values for hemoglobin reference standards vs. hemoglobin concentration.
Figure 18:
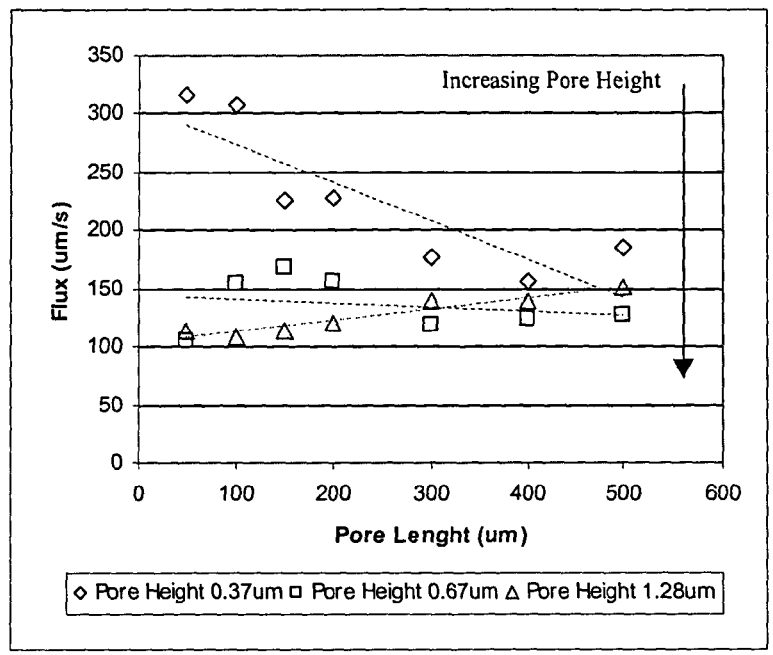
FIG. 18 is a plot of plasma filter flux vs. pore length for three different pore heights.
Figure 19:
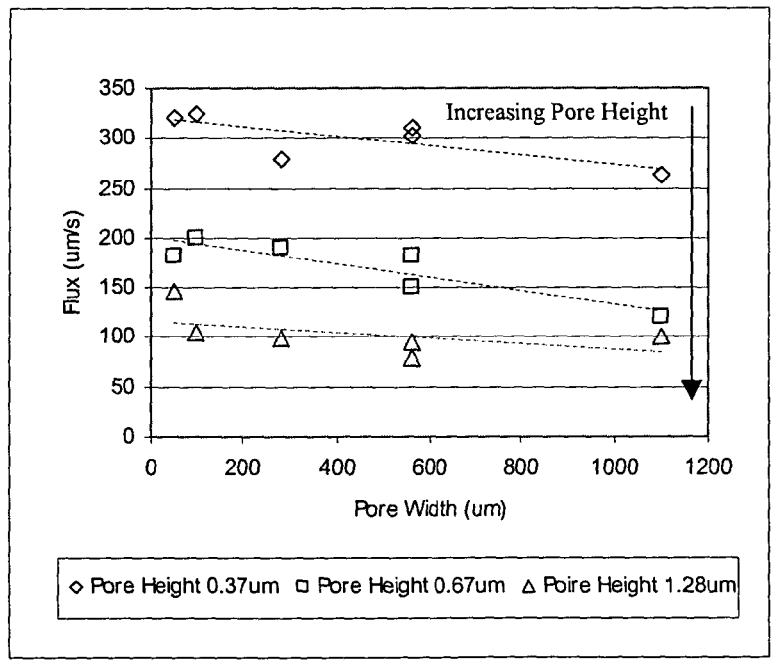
FIG. 19 is a plot of plasma filter flux vs. pore width for three different pore heights.
Figure 20:
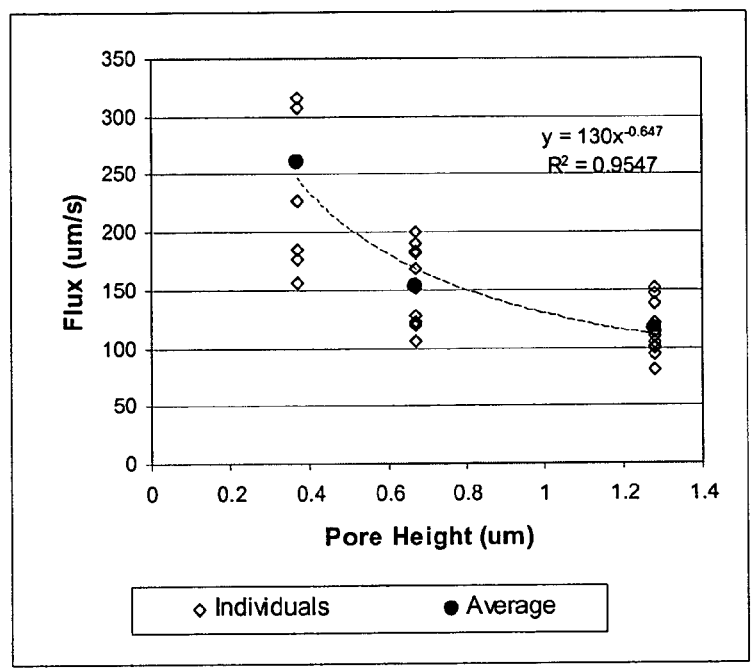
FIG. 20 is a plot of plasma flux vs. pore height for all individual microfilter tests and average flux at each value of pore height.

The four hemoglobin standards on each test wafer were photographed before and after device testing and digitally analyzed to determine the degree of red color, calculated as % Red pixel value. FIG. 15 shows all measured values of % Red for the four hemoglobin standards on all wafers. The hemoglobin concentration in the isolated plasma of each microfilter was determined based on the % Red pixel value. Three microfilters were tested at each level of pore height, width and length, and the average hemoglobin concentration was calculated. The hemoglobin concentrations versus pore height, width and length are shown in FIGS. 16 and 17. Additionally the effects of pore dimensions on plasma filtrate flux are shown in FIGS. 18-20. The average plasma flux was calculated based on an estimated operating time of 10 seconds for all devices, as the experimental methods were not capable or intended to measure blood flow rate and device operation time for each test.

An optical micrograph of a hemolysis test device with isolated plasma was taken from a test device with the largest pore height (1.28 μm). In these 1.28 cm pore height devices cells were observed to penetrate the filter area, and in some devices a few cells could be observed in the plasma filtrate.

Discussion

The effects of microfilter height, width, and length, on hemolysis were based on a colorimetric assessment of hemoglobin concentration in the extracted plasma. This on-wafer calorimetric measurement technique was originally developed as part of this research. The calorimetric assessment was calibrated using on-wafer hemoglobin standards as shown in FIG. 15. The correlation between % Red and hemoglobin concentration in the standards was evaluated for statistical significance using Anova, and the difference was found to be highly significant, $p<0.005$. This correlation demonstrates the validity of this colorimetric technique to measure hemoglobin in the isolated plasma.

The experimental data indicate that pore height and length effect hemolysis in microfilters while pore width was not significant (FIGS. 16-17). Pore height, or an equivalent De, was the primary modulator of hemolysis with larger pore heights producing higher levels of hemolysis. As can be observed in FIG. 17, the effect of pore length was modulated by pore height, as hemolysis was not sensitive to filter length at the smallest pore height. From a design standpoint, the data indicate that hemolysis is minimized at pore heights less than 0.5 um, and devices should be fabricated with the minimum filter length achievable by the fabrication process. The minimum pore length attainable using the equipment and techniques utilized in this study is approximately 20 um.

To consider the physical mechanisms responsible for hemolysis in microfilters, the effects of filter geometry on membrane stress and time at stress must be considered. As discussed previously, filter length can modulate the time required for plasma to cross the filter pore and reach the deeper outlet channel. During this time, stress on red cells at the blood-filter interface is highest due to the high capillary force generated by the filter pore. Once plasma reaches the outlet channel, stress on the red cells is greatly reduced, as the capillary pressure generated by the outlet channel is more than an order of magnitude less than the filter pore. In the experimental devices, this time was estimated by assuming that the filter pore must be completely filled with plasma before wetting the outlet channel. The time for plasma to cross the filter was estimated per the following equation, where t is the time to cross the filter, H, W and L are the filter pore dimensions of height, width and length, and J is the average plasma filter flux.

$$t = \frac{PoreVolume}{Flux * PoreArea} = \frac{H*W*L}{J*H*W} = \frac{L}{J}, \quad (2)$$

where t is the time to cross the filter, H, W and L are the filter pore dimensions of height, width and length, and J is the average plasma filter flux.

Figure 21:
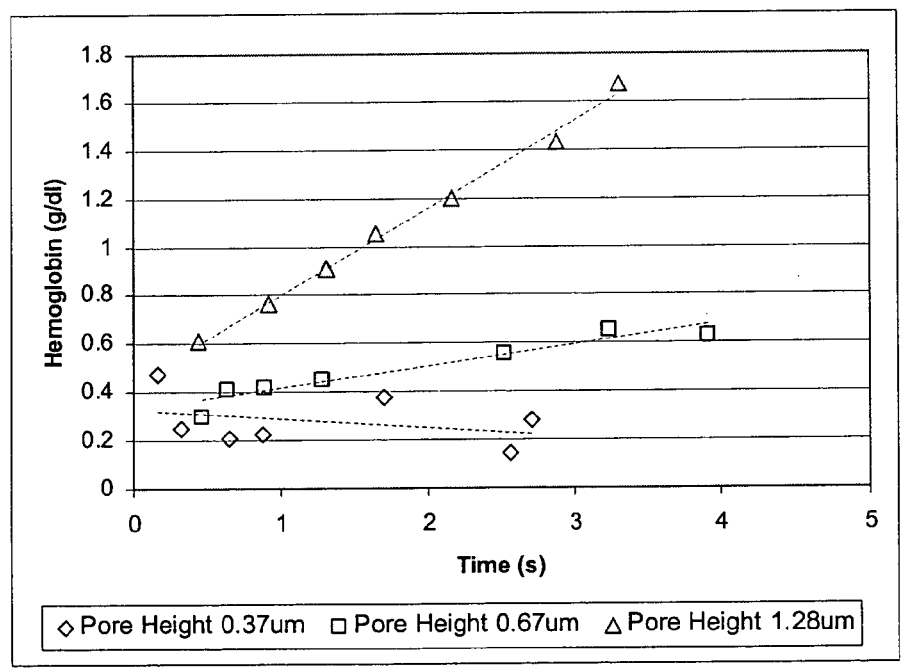
FIG. 21 is a plot of hemoglobin concentration in plasma vs. time for plasma to cross the filter.

Using this equation, the time required for plasma to cross the filter was calculated for the filter length test devices and compared to the concentration of hemoglobin in the filtrate, as shown in FIG. 21. The time required for plasma to cross the filter varied from a few hundred milliseconds up to ~4 seconds. Filter wetting time was similar among all test devices, and the effect of pore height on hemolysis cannot be attributed to differences in filter wetting time. However at large pore heights the level of hemoglobin in the plasma filtrate increases with time, and this result demonstrates that filter pore length has a secondary effect on hemolysis.

Figure 22:
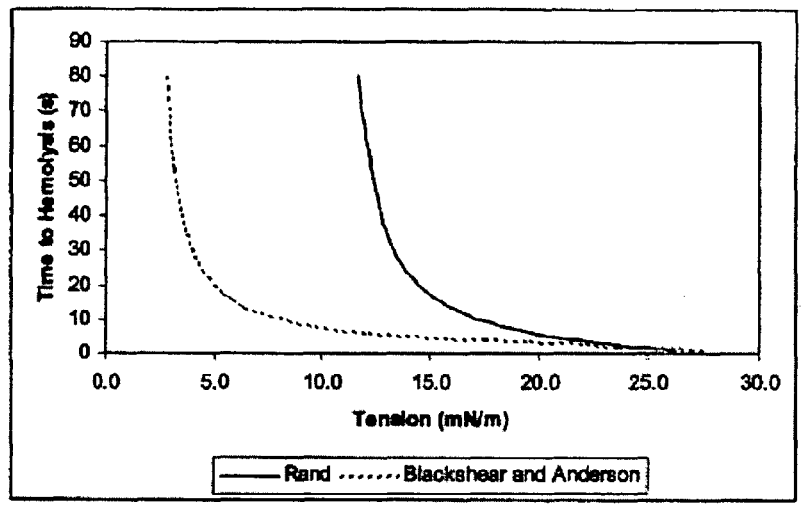
FIG. 22 is a plot of time to hemolysis vs. membrane tension as developed by Rand (1964) and Blackshear and Anderson (1977)

The other factor that controls hemolysis, membrane stress, was initially evaluated for the experimental devices following the approach of Rand, previously discussed in the theory section. In Rand's study the portion of the red cell entering the filter was treated as a hemisphere, and the membrane stress was estimated by equation $\sigma_m$, where $\sigma_m$ is the membrane tension, $h_p$ is half the pore height and the radius of the hemispherical portion of the cell in the filter, $R_c$ is the radius of the cell outside the filter, and $\Delta P$ is the transfilter pressure. Assuming the transfilter pressure is equivalent to the capillary pressure generated in the filter by plasma, the pressure is calculated per equation where $\sigma$ is the surface tension of plasma to air. For these conditions, $1/R_c$ is small compared to $1/h_p$ and equation $\sigma_m$ can be reduced to equation. Due to the interaction between pressure, pore height, and membrane stress, the pore height term cancels. This equation predicts that membrane stress is equal in all devices with a membrane tension on the order of ~35 mN/m. On the basis of the models and studies of Rand, and Blackshear and Anderson (FIG. 22), this is a very high level of membrane stress, and hemolysis should occur nearly instantaneously.

$$\sigma_m = \frac{\Delta P}{2\left(\frac{1}{h_p} + \frac{1}{R_c}\right)} \quad (3)$$

$$\Delta P = \frac{\sigma}{h_p} \quad (4)$$

$$\sigma_m = \frac{\sigma}{2} \quad (5)$$

Figure 23:
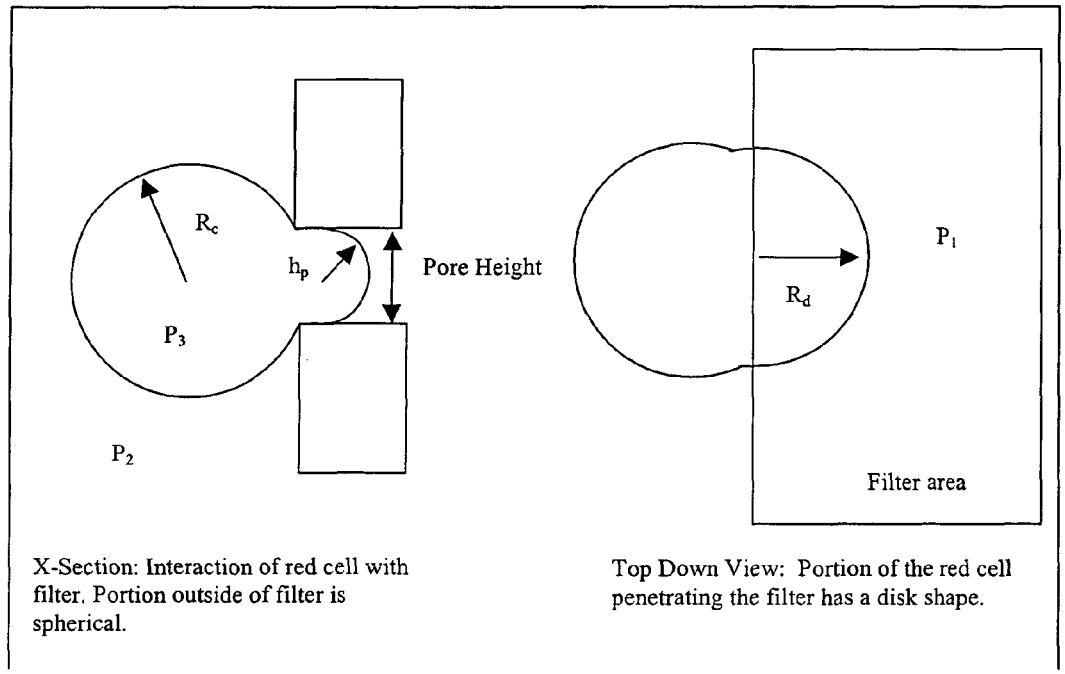
FIG. 23 is a representation of a model of red cell deformation into a rectangular microfilter pore, which model is used to estimate membrane tension.

Since Rand's methodology does not explain the effect of pore height on hemolysis observed in this study, the approach was modified to take into consideration the rectangular shape of the microfilter pore. In Rand's approach, the cell was assumed to deform into the filter pore with a hemispherical shape. This assumption is reasonable for a circular pore, but with rectangular pores, that are much wider than a single cell, this condition is unlikely. An alternative approach is to assume that cells deform into the filter pore with a disc shape as shown in FIG. 23. With this assumption, the membrane tension can be estimated per equations (6,7,8), where $P_2$-$P_1$ is the transfilter pressure. The dimensions of the deformed cell are estimated by assuming that the area and volume of the cell remain constant up to the point of hemolysis. The portion of the cell outside the filter is estimated as a sphere, and the portion of the cell in the filter is estimated as a semicircular cylinder. Using the values of cell area and volume reported by Skalak et al (1973), surface area 147 um$^2$ and volume 92 um$^3$, the cell dimensions and membrane stress were calculated as shown in Table 3.

$$P_3 - P_1 = \sigma_m\left(\frac{1}{h_p} + \frac{1}{R_d}\right) \quad (6)$$

$$P_3 - P_2 = \frac{2\sigma}{R_c} \quad (7)$$

$$P_2 - P_1 = \sigma_m\left(\frac{1}{h_p} + \frac{1}{R_d} - \frac{2}{R_c}\right) \quad (8)$$

TABLE 3

Membrane stress analysis based on cell deformation as a disk.

| Pore Height (um) | Cell Radius (um) | Disk Radius (um) | Membrane Tension (mN/m) |
|---|---|---|---|
| 0.2 | 2.789 | 3.7188 | 58.6 |
| 0.4 | 2.777 | 3.7184 | 61.6 |
| 0.6 | 2.765 | 3.7182 | 64.8 |
| 0.8 | 2.752 | 3.7181 | 68.5 |
| 1   | 2.740 | 3.7182 | 72.8 |
| 1.2 | 2.728 | 3.7185 | 77.6 |

Figure 24:
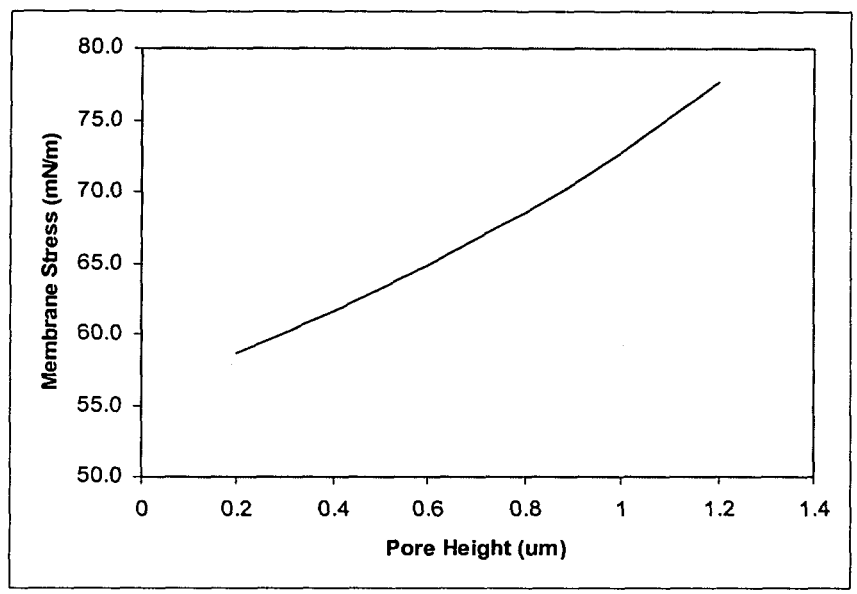
FIG. 24 is a plot of modeled membrane tension vs. pore height for red cell deformation in rectangular pores via capillary action.

This analysis indicates that membrane stress increases with increasing pore heights (FIG. 24). However, as with the previous analysis, the estimated membrane stresses are very high, which suggest that hemolysis should occur on a millisecond time scale in all devices. Neither model of membrane stress could account for the experimental dependency of hemoglobin concentration on pore height as observed.

In a study of hemolysis for membrane plasmapheresis, Zydney and Colton (1982) proposed that red cells occlude filter pores momentarily and then dislodge due to drag forces or interactions with other cells. They hypothesized that the residence time of a red cell in the filter pore was inversely proportional to shear rate, and therefore hemolysis was reduced at higher shear rate. Using this approach to investigate the correlation between pore height and hemolysis observed in this study, cell residence time is hypothesized to be a function of the area of the cell embedded in the filter pore and shear rate. The area of the cell in contact with the filter generates a "frictional" force that holds the cell in the filter, and shear rate at the filter modulates the release of the cell through drag forces or cell-cell interactions. The portion of the cell protruding in the filter is assumed to take on a disk shape with radius $R_d$, related to pore height by equation (9) where $k_1$ and $k_2$ are constants.

This equation predicts that the deformation of a cell into a filter pore reaches a minimum as pore height decreases. The area of cell in contact with the filter, $A_{contact}$, can be computed as shown in equation (10). Residence time of a cell, $t_r$, is proposed to be a function of shear rate and contact area as shown in equation (11), where c and k are constants. Under this model residence time of a cell in the filter is related to the square of the pore height, and shear rate as shown.

$$R_d = k_1 + k_2 h_{pore}^2 \quad (9)$$

$$A_{contact} = \pi R_d^2 \quad (10)$$

$$t_r = k\gamma^{cA_{contact}} \quad (11)$$

Figure 25:
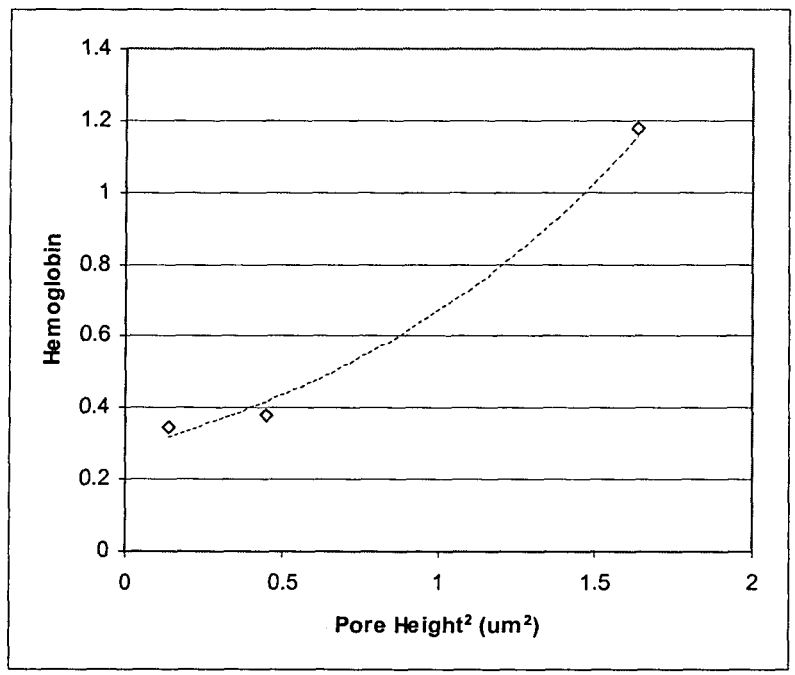
FIG. 25 is a plot of average hemoglobin concentration vs. pore height squared for all filter width tests.

At a constant membrane stress, this model predicts that significant hemolysis only occurs when cell residence time reaches a critical level. If residence time is modulated by pore height, a dramatic increase in hemoglobin is expected beyond a critical pore height, and this is observed in the experimental data. FIG. 25 shows the relationship between pore height squared and hemoglobin level for all pore width test devices, and demonstrates a dramatic increase in hemoglobin with pore height.

The effect of pore geometry on plasma flux may also be evaluated using a residence time model, and the results of this analysis also support the validity of this approach. Pore height was found to be a primary modulator of plasma flux, with decreasing pore height causing a significant increase in flux, while pore width and length did not have a clear and consistent effect. This result was unexpected, as pore size is not reported to have a significant impact on plasma flux in the plasmapheresis literature.

A residence time model can be used to explain the observed dependence of plasma flux on pore height. Under this hypothesis, plasma flow across the filter occurs between the time a red cell is dislodged from the filter and is replaced by a new cell. Flux is proportional to the ratio of the time the filter is unoccupied by cells and the total time of operation. This ratio may be modeled using an estimate of the residence time of red cells in the filter and the time required to replug the filter. The time to replug the filter is modeled as an inverse function of shear rate as shown in equation (12), where $t_p$ is the time for a new cell to plug the filter, and $c_5$ and m are constants. The overall equation for plasma flux can then be developed from equations (11) and (12) resulting in equation (13) Rearrangement and simplification of this equation results in a model for flux as shown in equation (14), where a, b, and k are constants and $\gamma_w$ is wall shear rate.

Figure 26:
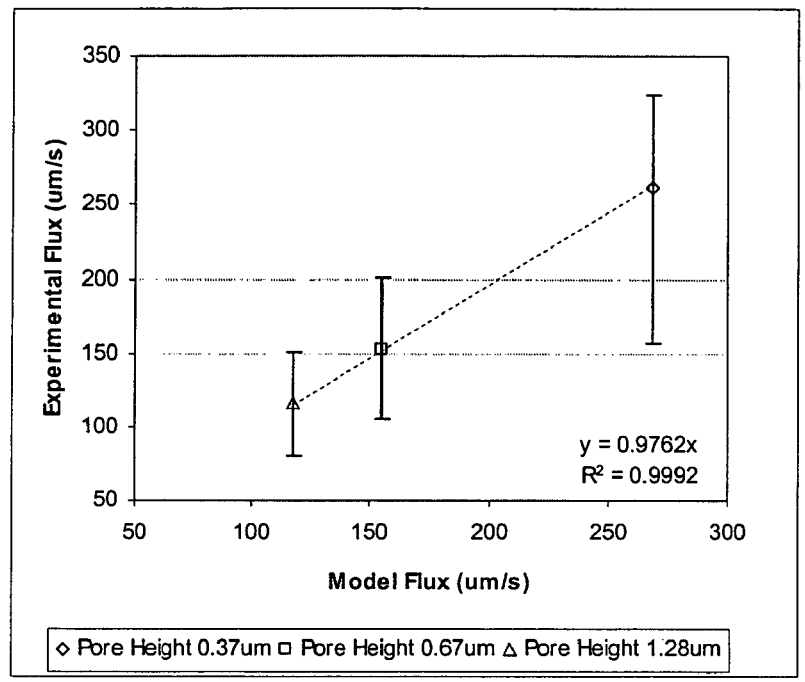
FIG. 26 is a plot of average experimental flux at three filter pore heights vs. residence time model of flux with error bars showing the range of experimental flux data.

A fit of this model to the average flux for all hemolysis test devices is shown in FIG. 26, and the correlation of the experimental data to the model supports the validity of a residence time approach.

$$t_p = c_5 \gamma^m \quad (12)$$

$$J_f = k_1 \frac{\text{time pore is open}}{\text{total time}} \quad (13)$$

$$= k_1 \frac{t_p}{t_p + t_r}$$

$$= k_1 \frac{c_5 \gamma^m}{c_5 \gamma^m + c_3 \gamma^{c_4} A_{contact}}$$

$$J_f = k \gamma_w^{(a+b h_{pore}^2)^2} \quad (14)$$

The effects of pore height in microfilter plasmapheresis suggest that the physical mechanism of plasma separation and hemolysis are significantly different from membrane plasmapheresis. This difference is likely attributable to two major differences in separation characteristics. First, microfilter membranes are rectangular, and the interaction of the cell with the filter is substantially different than the more circular microporous membrane pores. Secondly, micro filter pores are located at a singular position in the channel, while microporous membrane pores cover the entire area of the flow channel. In a conventional membrane separation operation utilizing flow channels of greater length scale i.e., meter scale, a single trapped red cell in the filter pore is typically surrounded by a localized boundary layer of concentrated red cells. This boundary layer of hydraulically resistive packed cells self-limits the flow of filtrate subfraction. Generally known as "concentration polarization" in the separation science and engineering field that design macro-filtration devices, the hydraulically resistive boundary layer thickness is relatively small compared to flow channel dimensions and thus bulk flow-induced momentum interactions with the boundary layer are somewhat limited. In the microfilter operation, however, blood is freely flowing under the filter pore area, the relative thickness of the boundary layer compared to the microflow channel dimension can be significant. In this smaller scale separation device, trapped red cells at the filter face may have significant interactions with the bulk flow stream that are not possible in conventional membrane separation processes, such as reverse osmosis, ultrafiltration and the microfiltration of complex fluids such as plasmapheresis.

From the foregoing it will be seen then, that the major microfilter design parameters controlling hemolysis in microfluidic-based passive blood separation devices have been identified. Hemolysis is minimized at pore heights <0.5 μm and filter pore lengths <100 um. Surprisingly, plasma flux was substantially increased at shallow pore heights. This was contrary to the common perception involving membrane filtration. This is a very favorable result for microfilter device as hemolysis is minimized while flux is maximized at small pore heights. The relationship between both flux and hemolysis with filter pore heights may be explained utilizing a residence time model. In this model, cell residence time in the filter is controlled by cell deformation into the filter pore, which is minimized at low pore height.

The controlled lysis of red cells was accomplished by varying the height and length of the filter pore was achieved. This indicates that this technique may be applied to lab-on-a-chip applications where the controlled lysis of target cells is desired. The possibility of the selective lysis of other bloods cell fractions, e.g. white blood cells, from a drop of whole blood is suggested, as well. If such devices could be developed, they would have significant implications in the development of integrated lab-on-a-chip device utilizing miniaturized on-chip Polymerase Chain Reaction (PCR) methods for genomic and proteomic applications as these devices could selectively lyse white blood cells directly from whole blood.

Several diagnostic possibilities present themselves as an outgrown of the above development. The susceptibility of red cells to lysis is a diagnostic technique used in diagnosing certain disease states such as heredity spherocytosis and thalassemia. Diagnostic testing for these conditions is typically performed using a technique known as "osmotic fragility." This test determines the susceptibility of red cell lysis in various concentrations of saline by detecting the release of hemoglobin from lysed red cells. This technique is cumbersome and time consuming. It requires evaluation of a small blood sample in 10 to 20 different concentrations of saline solution which must be individually prepared.

In this example, the determination of red cell fragility is conducted using the passive microfluidic device described, and the test takes several minutes. A drop of blood is placed on the inlet reservoir and proceeds to flow through the microchannel for exposure to 5 to 20 individual microfilters of various lengths as illustrated in FIG. 7. Each individual microfilter extracts a small amount of plasma into a plasma outlet channel. The level of stress applied to the blood cells by each microfilter is determined is determined by the length of the microfilter. Longer microfilters apply a greater level of stress. Using a colorimetric technique, the plasma isolated by each microfilter is analyzed for the concentration of hemoglobin. As the level of cell lysis increases the amount of hemoglobin and isolated plasma increases and the degree of red coloration of the isolated plasma can be detected by calorimetric comparison of the isolated plasma to several on-device hemoglobin standards.

A further example of the use of devices of the present invention includes the detection of Sickle cell anemia. sickle cell anemia is a genetic blood disorder that causes anemia and pain. This disease is caused by the presence of defective hemoglobin in the blood cells known as hemoglobin s (Hbs). The presence of Hbs causes the red blood cells to become more rigid and taken on a classic sickle cell shape. "Unlike normal red cells, the sickled red cells cannot squeeze through small blood vessels. They stack up to cause blockages depriving organs and tissues of oxygen-carrying blood. This produces periodic episodes of pain and can lead to damage of tissues and vital organs as well as to other serious medical problems. While normal red blood cells live about 120 days in the bloodstream, sickled red cells die after 20 to 20 days. Because they cannot be replaced fast enough, the blood is chronically short of red blood cells, the condition known as anemia."

Sickle cell diagnosis is typically done using electrophoresis techniques to identify the presence of Hbs. This is a complex technique requiring significant sample preparation, skilled labor and expensive diagnostic equipment. Here, a drop of blood is placed on the inlet to a microfluidic channel comprised of a series of microfilters of varying height from 0.8 μm to perhaps 2 μm. Plasma and red blood cells are isolated in the outlet area of the various filters. Analyzing using calorimetric techniques based on the presence of hemoglobin, sickle cells with reduced deformability and unable to pass across filter dimensions that normal red blood cells may pass will greatly reduce the degree of red coloration in the filter effluent in sickle cell patients.

Changes in Blood Flow-Deformation Behavior

The present technology can be used to discriminate changes in the flow-deformation behavior of complex fluids such as blood. Using more macroscale devices, known as viscometers or rheometers, Dintenfass previously showed that even small changes in blood-related flow-deformation parameters such as, for example, viscosity's correlation to pre-disease and diseased states.

The present microfluidic devices have the potential capability and fidelity to discriminate small changes in blood flow behavior that may also be useful for the diagnosis of pre-disease, disease and other pathological states expressed via viscosity and related flow-deformation characteristics of complex biological fluids such as blood. One example is, again, Sickle Cell Anemia where the red blood cells take on the characteristic sickle cell shape, the effect of which can be seen in the flow-deformation behavior of blood.

Monitoring Capillary Pressure

Figure 10:
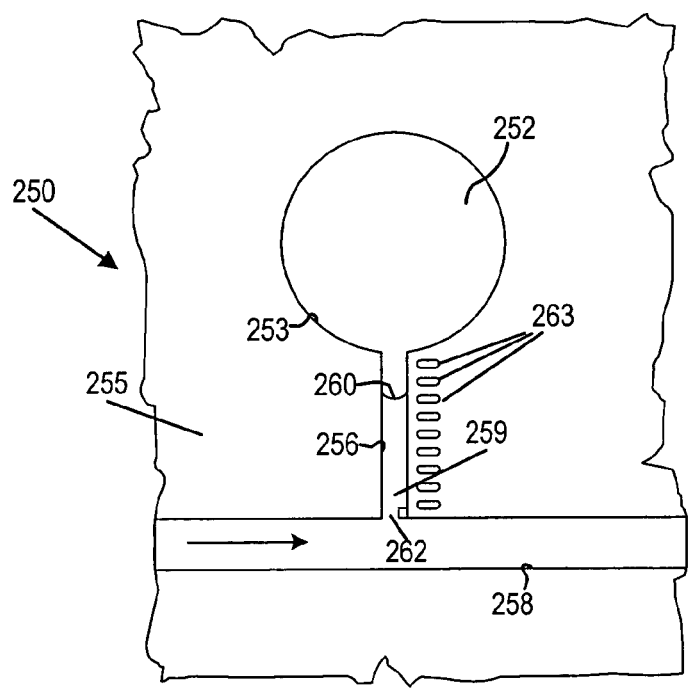
FIG. 10 is a capillary pressure gauge having entrapped air acted on by a column of fluid.
Figure 11:
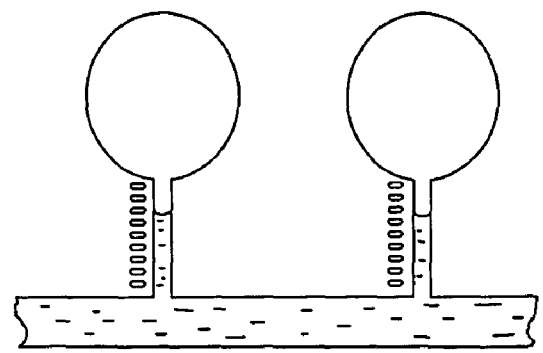
FIG. 11 is a schematic illustration of a flow meter made up of two of the capillary pressure gauges of FIG. 10.

Shown in FIG. 10, a gauge 250 for monitoring capillary pressure includes an entrapped air bubble 252 encapsulated in a small chamber 253 etched in the Si of a substrate 255. A tiny tube 256 communicates between the chamber 253 and a flow channel 258, like the channels previously discussed. A column 259 of the specimen liquid in the tube 256 acts against the pressure of the entrapped air. The position of the meniscus 260 along the tube 256 is a measure of capillary pressure of the liquid in the channel 258 and tube 256. A constriction 262, of the nature of a filter pore, for example, may be required or efficacious to prevent air escaping the chamber 253 during initial wetting of the channel 258 and the tube 256. Indicia 263 may be etched into the substrate 255 or printed on the glass of a cover plate through which the gauge 250 is viewed.

As shown in FIG. 1, two of the "bubble meters" of the kind illustrated in FIG. 10 can be placed a known distance apart. Similar to a pitot tube, the pressure difference at the two locations is measured. The pressure drop along a long length of flow channel is thus known and from that flow rate of a know liquid can be estimated.

Fabrication

Microfluidic devices were fabricated in 100 mm diameter silicon and glass wafers. The filter structures and flow channels were etched into silicon wafers, and enclosed by anodically bonding a glass wafer to the silicon wafer. The fabrication process can be broken down into five main areas: photolithography, silicon etching, cleaning, oxidation, and anodic bonding. A summary of the process details for each area is provided below, and a detail step-by-step process is provided in Table 4. A detailed list of the chemicals utilized is provided in Table 5, and equipment detail is provided in Table 6.

TABLE 4

Step-by-step fabrication detail for microfilter devices.

| Process | Parameters | Time | Equipment | Comments/Notes |
| --- | --- | --- | --- | --- |
| Pattern Filter Area | | | | Starting material: 100 mm silicon wafers |
| Dehydration Bake | 95° C. | 2 min | Oven | |
| HMDS Application | 4000 RPM | 30 sec | Spinner | |
| Resist Application | 4000 RPM | 30 sec | Spinner | Dispense 1-2 ml resist, ~1 μm thick |
| Soft Bake | 80° C. | 15 min | Oven | |
| Exposure | Contact print | 15 sec | Canon | Test exposure and adjust as required |
| Develop in Beaker | Developer | ~3 min | Wet Bench | Over develop by 50% |
| DI Rinse | | | Sprayer | |
| $N_2$ Dry | | | $N_2$ Gun | |
| Hard Bake | 95° C. | 2 min | Oven | Dry wafer |
| Measurement | | | Dektak | Pre-measurements for etch |
| Filter Etch | | | | |
| Plasma Etch $SF_6$ | See Table A.5 | | Plasma Lab | Adjust etch time to meet target |
| Measurement | | | Dektak | Verify etch depth meets target |
| Clean | | | | |
| Strip Resist | Microstrip | ~5 min | Hot plate | Heat stripper ~40-50 C, use agitation |
| Sulfuric Clean | 95° C. | 10 min | Wet Bench | Spike sulfuric tank with ~200 ml peroxide |
| Rinse/Dry | | | $QDR/N_2$ | 4 cycle quick dump rinse cycle, dry with $N_2$ |

TABLE 4-continued

Step-by-step fabrication detail for microfilter devices.

| Process | Parameters | Time | Equipment | Comments/Notes |
|---|---|---|---|---|
| Pattern Channels | | | | |
| Dehydration Bake | 95° C. | 2 min | Oven | |
| HMDS Application | 4000 RPM | 30 sec | Spinner | |
| Resist Application | 4000 RPM | 30 sec | Spinner | Dispense 1-2 ml, ~1 μm thick |
| Soft Bake | 80° C. | 15 min | Oven | |
| Exposure | Contact print | 15 sec | Canon | Align mask to filter pattern |
| Develop in Beaker | Developer | ~3 min | Wet Bench | Over develop by 50% |
| DI Rinse | | ~30 sec | Sprayer | |
| $N_2$ Dry | | | $N_2$ Gun | |
| Hard Bake | 95° C. | 2 min | Oven | |
| Measurement | | | Dektak | Pre-measurements for etch |
| Etch Channels | | | | |
| Plasma Etch $SF_6$ | See Table A.5 | | Plasma Lab | Adjust etch time to meet target |
| Measurement | | | Dektak | Verify etch depth meets target |
| Clean | | | | |
| Strip Resist | Microstrip | ~5 min | Hot Plate | Heat stripper ~40-50 C, use agitation |
| Sulfuric Clean | 95° C. | 10 min | Wet Bench | Spike sulfuric tank with ~200 ml peroxide |
| Rinse/Dry | | | QDR/$N_2$ | 4 cycle quick dump rinse cycle, dry with $N_2$ |
| Measurement | | | Dektak | Measure main channel and filter depth |
| Wet Oxidation | | | | |
| Wet Oxidation | 1050° C. | ~80 min | Furnace | Steam oxidation, target ~2100 Å |
| Measure Thickness | | | NanoSpec | Measure oxide thickness |
| Prepare Glass | | | | |
| Drill Access Holes | Glass Wafers | | Dremel | Dremel drill press, and diamond tipped bits |
| Clean Wafers | | | | |
| Organic Clean | Microstrip | ~5 min | Hot plate | Heat until warm to touch, agitate frequently |
| Sulfuric Clean | 95° C. | 60 min | Wet Bench | Spike sulfuric tank with ~200 ml peroxide |
| Rinse/Dry | | | QDR/$N_2$ | |
| Anodic Bonding | | | | |
| Align Wafers | | | | Visually align wafers by hand |
| Bonding | ~550° C., ~2000 VDC | 15 min | Hot Plate/DC Power Supply | Process until wafers are completely bonded |

TABLE 5

Typical chemicals and materials used in microdevice fabrication.

| Chemical | Trade Name | Purpose | Supplier |
|---|---|---|---|
| Sulfuric Acid | Sulfuric Acid Semi Grade | Cleaning | Ashland Chemical (Columbus, OH) |
| Hydrogen Peroxide | Hydrogen Peroxide Semi Grade | Mix with sulfuric acid for cleaning | Ashland Chemical (Columbus, OH) |
| Photoresist | OCG 825 27CS | Photolithography | Arch Chemical (Norwalk, CN) |
| Photoresist Developer | OCG 945 developer | Development of exposed photoresist during photolithography | Arch Chemical (Norwalk, CN) |
| Organic Resist Stripper | Microstrip 2001 | Removal of exposed photoresist | Arch Chemical (Norwalk, CN) |
| 100 mm Glass Wafers, 1.1 mm Thick | Borofloat | Device substrate | Technical Glass Products (Painesville Twp., OH) |
| 100 mm Silicon Wafers, 0.5 mm Thick | Silicon | Device substrate | Wacker (Portland, OR) both <100> and <111> wafers with various doping levels have been used successfully |
| Hexamethyldisilizane | Adhesion Promoter | Resist adhesion | Arch Chemical (Norwalk, CN) |

TABLE 6

Equipment detail for microdevice fabrication.

| Equipment | Manufacturer | Model | Purpose |
|---|---|---|---|
| Wet Bench | Custom | | Cleaning, photoresist development, and removal |
| Heated, Quartz Lined Chemical Tank | PCT Systems (Fremont, CA) | 90 | Controlled heating of sulfuric/hydrogen peroxide solutions for cleaning |
| Resist Spinner | Specialty Coating Systems (Indianapolis, IN) | P6204 | Resist coating |
| Bake Oven | Blue M (Williamsport, PA) | | Resist baking |
| Photolithographic Contact Aligner | Canon (Lake Success, NY) | PLA-501 F | Exposure of photoresist using photomask |
| Photolithographic Contact Aligner | Suss Microtec (Waterbury Center, VT) | MJB 3 | Exposure of photoresist using photomask |
| Reactive Ion Etcher | Oxford Instruments (Concord, MA). | Plasma Lab Micro RIE 80 | Silicon etching |
| Hot Plate | Various | | Heating of organic resist stripper, anodic bonding |
| Spin-Rinse-Drier | Verteq (Santa Ana, CA) | 1600-44 | Rinsing of wafers after cleaning |
| Surface Profiler | Sloan Technology/Veeco Instruments (Woodbury, NY) | Dektak IIA | Measurement of device channel heights and widths |
| Film Thickness Analyzer | Nanometrics (Milpitas, CA) | NanoSpec AFT | Measurement of resist thickness and silicon oxide layers |
| Oxidation Furnace | Amtech Systems (Tempe, AZ) | Tempress 8 Stack | Growth of thermal oxide on silicon |
| High Voltage DC Power Supply | LKB Instruments (Rockville, MD) | LKB 2103 | Anodic Bonding |
| Surface Thermometer | PTC Instruments (Los Angeles, CA) | 573C | Monitoring temperature during anodic bonding |

Photolithography

Figure 5:
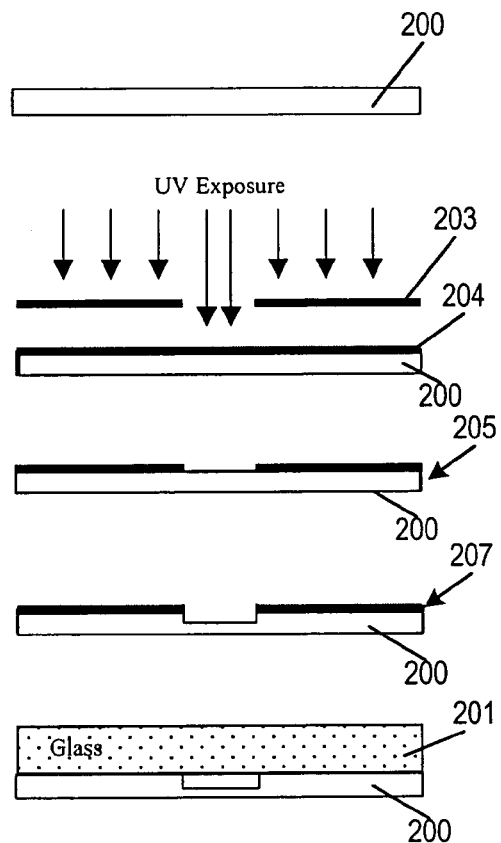
FIG. 5 is a diagrammatic illustration of the steps in the formation of a fluid handling device like the filter of FIG. 1.

Photolithography was utilized to etch the filter pore and flow channel patterns into the silicon wafer using reactive ion etching. Two masking layers or masks 203 (FIG. 5) are required to define a microfilter, the shallower first layer patterns the filter pore structures, and the second masking layer, aligned to the first pattern, defines the flow channels. Positive photoresist was utilized with a dark field photomask to perform these operations.

The photolithographic process starts by baking the wafer in a convection oven for several minutes at 95° C. to remove moisture. After the initial bake, hexamethydisilazane (HMDS) is applied to improve resist adhesion. About 0.5 ml of HMDS is applied to the silicon wafer, and the wafer is spun using a spin coater at ~4000 RPM for 30 sec to spread the HMDS across the wafer. After HMDS application, ~1-2ml of photoresist 204 is dispensed on the center of the wafer. Again using the spin coater, the wafer is spun at 4000 RPMs for 30 seconds to spread the resist evenly across the wafer. After spin coating, the wafers are baked in a convection oven (soft bake) at 80° C. for 15 minutes to remove solvents from the resist and improve mechanical stability of the film. Soft bake time and temperature are important as these factors affect the photospeed of the resist, i.e. high temperatures will destroy the photoactive components of the resist.

Using a photomask 203, selective areas of the resist-coated wafer are exposed with ultraviolet light (UV) in a contact aligner, thereby transferring the mask pattern to the photoresist. The UV exposed photoresist is selectively removed as shown at 205 by immersing the wafer in a beaker of photoresist developer solution. The wafer is gently agitated during development, and the development time is determined by a visual assessment of the wafer. After development, the wafers are rinsed with DI water, and dried using a nitrogen $N_2$) gun. Wafers are then baked in a convection oven to ensure all water is removed, remove solvents, and improve mechanical stability of the film (hard bake). After the hard bake, the wafer is ready for etching or other selective manipulation of the wafer surface.

Silicon Etching

Lithographic patterns are transferred to the silicon wafer using reactive ion etching with sulfur hexafluoride ($SF_6$) as indicated at 207. Prior to the silicon etch step, a brief silicon oxide etch is performed using a $CF_4$ and oxygen, $O_2$, plasma to help remove native oxide on the silicon surface. The main silicon etch is then performed using $SF_6$. Typical etch conditions are provided in Table 7.

TABLE 7

Typical silicon plasma etch process

| Step | Purpose | Gas (sccm) | Power (watts) | Pressure (mTorr) | Time (min) | Notes |
|---|---|---|---|---|---|---|
| 1 | Pump Down | None | 0 | 0 | Wait | Pump down to minimum pressure. |
| 2 | Oxide Etch | 3 O$_2$ 3 CF$_4$ | 120 | 75 | 2 | This brief oxide etch intended to remove native oxide. Wait for gas and pressure to stabilize prior to turning on RF. |
| 3 | Pump Down | none | 0 | 0 | Wait | Wait for minimum pressure. |
| 4 | Silicon Etch | 25 SF$_6$ | 120 | 20 | Various | Etch time adjusted to meet experimental targets. Wait for gas and pressure to stabilize prior to turning on RF. Etch rate ~0.8 um/min on N-type <100> silicon |
| 5 | Pump Down | None | 0 | 0 | Wait | Pump out chamber prior to venting. |
| 6 | Vent | N$_2$ | | | Wait | Automatic equipment cycle, pumps down chamber and then vents to atmosphere with nitrogen. |

Wafer Cleaning

Cleaning is a critical step in device fabrication. Debris or other contaminants left on the wafer can act as an etch mask and ruin the lithographic pattern. Additionally, particulates and organic contamination can prevent uniform bonding of silicon to the glass. In this fabrication process, cleaning was accomplished using a commercial organic stripper (Microstrip 2001) and a hot solution of sulfuric acid and hydrogen peroxide (piranha).

The organic stripper is used to remove photoresist and organic contaminates. Wafers are immersed in a beaker of the warm stripper, ~40-50° C., and gently agitated. Agitation of the solution greatly improves cleaning, and helps to reduce process time. When cleaning resist from wafers, visible resist debris will appear in the cleaning solution. Wafers should not be removed from the organic stripper until all resist debris is broken down, or this material will contaminated the wafer when it is removed from solution. After cleaning with the organic stripper, wafers were cleaned in a mixture of hot sulfuric acid and hydrogen peroxide, ~95° C. This solution is maintained in a temperature-controlled tank by CSSER personnel. Approximately 200 ml of hydrogen peroxide was typically added to the sulfuric tank immediately prior to cleaning wafers.

Rinsing and drying of the wafers after cleaning is critical, a thorough rinsing with DI water helps to remove particulates. Particulates allowed to dry to a wafer are very difficult to remove. After cleaning in hot sulfuric, wafers were rinsed in quick-dump rinser (QDR) for four cycles, and then dried using a nitrogen gun.

The photolithography steps are performed twice; once for the shallower filter pores and once for the deeper flow channels.

Oxidation

Figure 12:
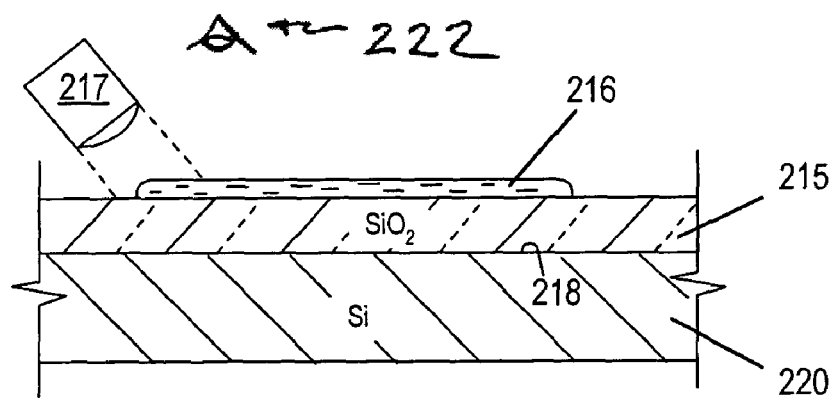
FIG. 12 is a schematic illustration of an optical arrangement for viewing otherwise transparent fluid moving on a surface.

Wafers were oxidized to improve the visibility of liquids in the microfluidic channels. As illustrated in FIG. 12, thin oxide layer 215, 2100A, on the silicon surface alters an optical interference effect that changes the color of the wafer. When a liquid wets this surface, the critical angle of reflection is changed, and the observed color of the surface changes visibly. This greatly improves visualization of fluid flow via capillary action in very shallow channels. Wafers were oxidized using an oxidation furnace in steam at 1050° C.

Light from a source 217 impinges the oxide layer 215. Depending on the angle of incidence, the light will be partially reflected and the refracted portion will emerge after reflection from the interface 218 between the silicon and silicon dioxide layer to interact with the reflected portion of light. A clear specimen 216 alters the critical angle and, depending on the angle at which the illuminating source 217 is supported can either eliminate the interference effect that altered the appearance of the silicon dioxide layer 215 or create an interference pattern if one was not present previously. The change effected by the clear specimen 216 in the interference perceived by an observer 222 makes the presence of the specimen 216 apparent.

Wafer Bonding and Glass Preparation

Glass wafers 201 are anodically bonded as closures to the patterned silicon wafers. Prior to bonding, multiple access holes (such as the holes 45, 52 and 55 of FIG. 1), ~1 mm diameter, are drilled through the glass wafer using diamond tipped drill bits (similar to dental drill bits), a Dremel tool, and Dremel drill press. Prior to drilling, the glass wafer is adhered to a metal substrate with double-sided foam tape. This helps to dampen vibration in the glass and prevent fracture. The foam tape also provides a cushion to the wafer, and minimizes stress points that occur due to particulates on the glass. The mounted wafer is submersed in a pan of shallow water to cool the bit during drilling. Glass wafers are very susceptible to breakage, and drilling must be done slowly with minimal applied pressure. Drilling is done using a pulsed action of the drill bit. The pulsed action prevents excessive heating of the bit, which improves bit lifetime. The diamond coating is degraded by heat, and lifetime of a bit is marginal, ~50 holes. After drilling the wafer is released from the foam tape by soaking in isopropyl alcohol. This procedure has been used to successfully drill ~75 holes in a single glass wafer.

Prior to bonding the glass must be cleaned thoroughly to remove particulates and other contaminates. Cleaning is performed using the organic stripper and hot sulfuric/peroxide as previously described. After cleaning, the silicon and glass wafers are aligned by hand and pressed together at a single contact point to establish a preliminary bond. A small amount of room temperature contact bonding will occur if the two surfaces are clean and flat. If a preliminary bond cannot be established, or if significant grinding sounds are heard when the wafers are contacted, the wafer pair is unlikely to bond using anodic bonding. Wafers should be re-cleaned as necessary until a preliminary room temperature bond can be achieved.

Figure 14:
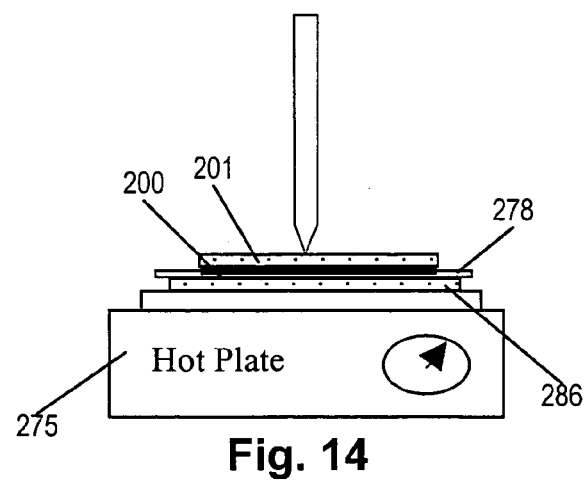
FIG. 14 is a diagrammatic illustration of anodic bonding equipment used to bond a glass closure or lid onto a silicon substrate.

After cleaning and preliminary bonding, the wafer is transferred to a hot plate, 275, for anodic bonding, in known fashion, as shown in FIG. 14. Anodic bonding occurs due to electrically induced movement of sodium ions in the glass away from the glass/silicon interface. A positive voltage is applied by an electrode 278 to the silicon wafer 200 and a negative voltage or ground is applied to the glass wafer 201 by an electrode 280. The silicon wafer is biased by placing it on the metal electrode 278 isolated from the hot plate surface using a glass plate 286. The glass wafer is biased using a heavy copper grounding rod with a pointed tip as the upper electrode 280. The wafer is heated to ~550° C. and up to 2000V is applied across the electrode 278, 280. Higher temperature and voltages increases the mobility of sodium ions and speed the bonding process, however bonding may be achieved at lower temperatures and voltage levels. The bonding process typically starts at a single contact point on the two wafers and spreads across the whole surface over time. Some un-bonded areas should be expected on every wafer-pair due to the presence of particulates or contamination. The quality of the cleaning technique used on the silicon wafers throughout the fabrication process has a large impact on the number of bonding defects present in the final devices.

Comparison with Membrane Plasmapheresis

Figure 27:
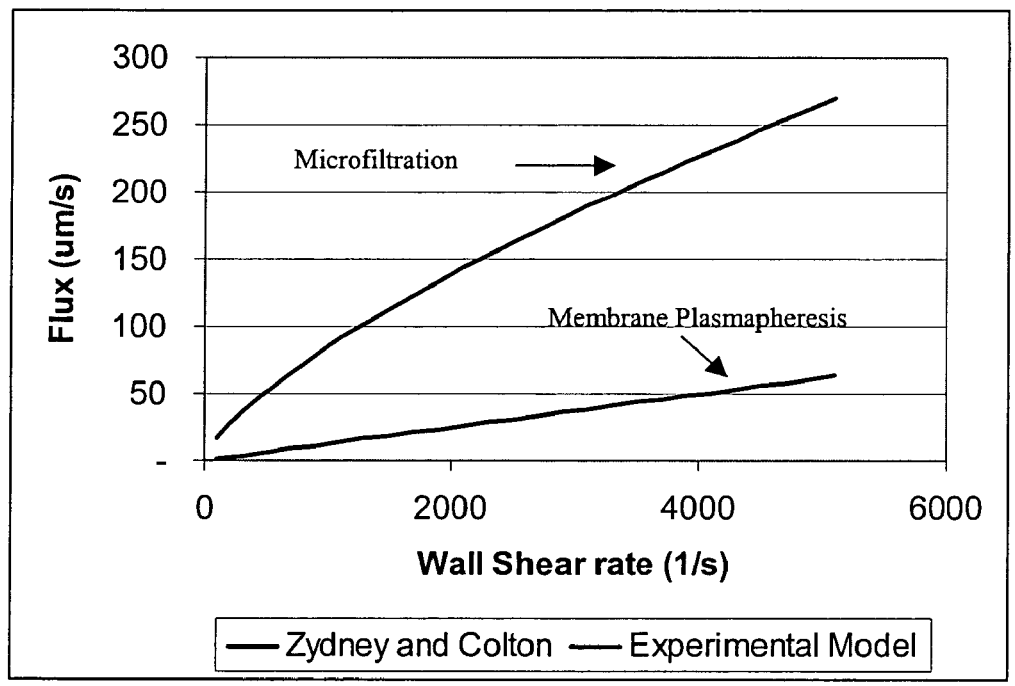
FIG. 27 is a plot of plasma flux vs. wall shear rate as previously described for membrane plasma pheresis and as observed for microfiltration of the experimental model according to the invention.

Passive microfilter device operation has similarities with microporous membrane plasmapheresis. For example, similar to microporous membrane, microfilter plasma flux is dependent upon wall shear rate raised to a fractional power and over the experimental range, the shear rate exponent varies between 0.55 and 0.76. This falls well within the range of exponent values reported for microporous membrane plasmapheresis. To compare the relative flux levels achieved in microfilter device tests to macroscale plasmapheresis performance, the model established by the experimental data obtained by the inventors was compared to the microporous membrane filtration model of Zydney and Colton, equation as shown in FIG. 27. On the basis of the model predictions, significantly greater microfilter plasma flux levels can be achieved (on the order of 2-5× higher) than can be achieved with microporous membrane systems. The surprisingly higher level of flux achieved in microfilter systems may be attributable to the significant physical differences between the two systems. Equations 15 and 16 represent the generalized and specific device plasma transport/flux performance heuristic that leads to the unexpected result shown in FIG. 27.

$$J_f = k \gamma_w^{(a+bH_{pore}^2)^2} \quad (15)$$

$$J_f = 0.62 \gamma_w^{(0.885 - 0.166 H_{pore}^2)^2} \quad (16)$$

The key difference between these two systems may be due to the filter pore distribution which is hypothesized as the primary factor responsible for the higher level of plasma flux in the microfilter system over the membrane process. In microporous membrane processes, a continuous fouling layer is formed over the entire surface of the blood-filter interface, and the interaction of the membrane with the bulk channel flow is limited to the outer surface. However, in weir style microdevices, the singular location of the filter pores at the top corner of the flow channel allows for greater interaction between the filtration channel blood flow and the fouling layer. Also, the filtration channel blood flow in microfilter devices surrounds the boundary layer on two sides, i.e. at the outer edge and underneath the fouling layer. This additional interaction with the surrounding bulk flow may increase plasma flux by reducing the fouling effect of the cells through decreased red blood cell residence time in the filter pore, or possibly an increased shear enhanced diffusion of red cells resulting in a decreased in boundary layer thickness, or both.

In membrane plasmapheresis, the effect of hematocrit on flux is well noted in the literature. The theoretical models decrease in plasma flux with increasing hematocrit. However, as mentioned, microfilter plasma flux was not significantly modulated by hematocrit between 19 to 40%. While the reason for this difference is unknown and warrants further characterization, this surprising insensitivity is inherently advantageous to clinical applications where significant sample-to-sample variations in hematocrit are present.

A Generalized Device Operational Model

Device modeling was performed in two stages. First, the blood flow through the device was modeled to estimate both the average wall shear rate in the filtration channel, as well as, the time of operation. Secondly, plasma flux was calculated based on the average wall shear rate. Using this result, the total volume of plasma extracted would then be calculated based on flux, microfilter dimensions, and the time of operation.

In the operational model, blood flow through the devices was predicted with classical hydrodynamic models assuming constant apparent viscosities for blood in the main filtration channel and the expanded channel. This methodology has limited utility, but in the absence of more comprehensive flow models that accurately predict the complex behavior of capillarity-driven blood flow, this method enables basic microdevice blood flow predictions, which are requisite to overall operational model development.

An assumed blood viscosity of 0.003 Pa-s in the main flow channel and an assumed blood viscosity of 0.040 Pa-s in the expanded channel were based on the experimental observations. Both of these assumed viscosities are consistent with blood having nominal hematocrit values in the range of ~35-45%. Device modeling for blood with hematocrit levels outside this ranges will require adjustment to these assumed apparent blood viscosity parameters.

Figure 28:
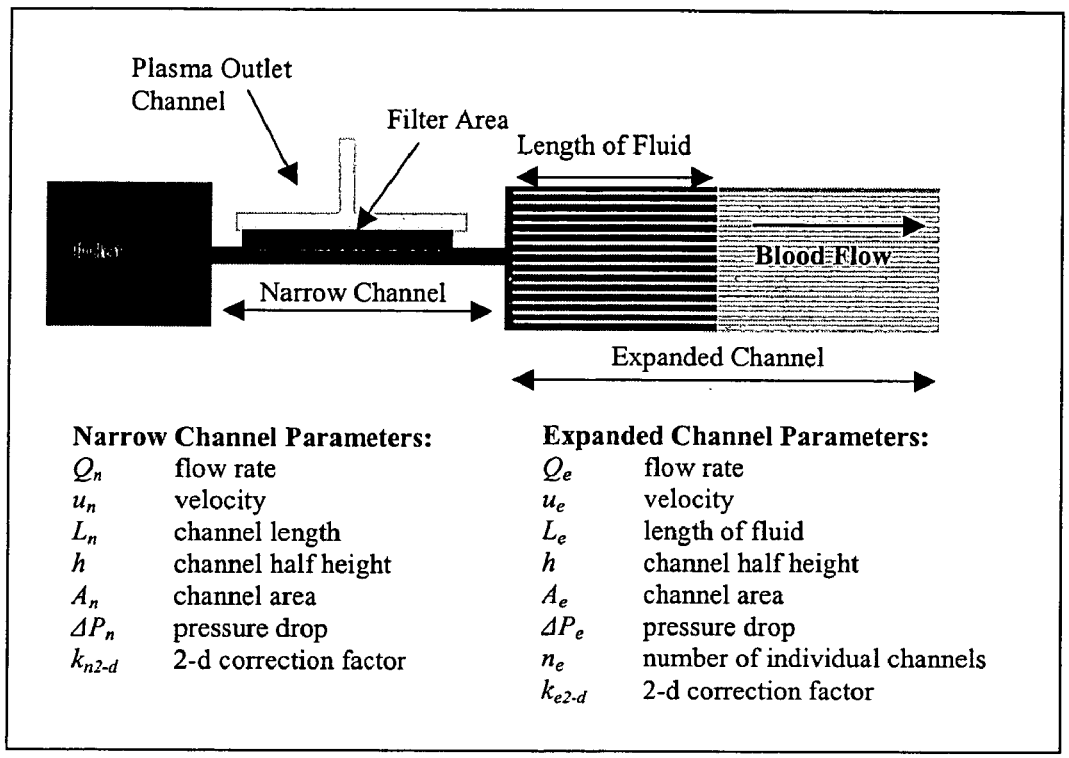
FIG. 28 is a diagrammatic illustration of a generalized microfilter in accordance with the invention and lists parameters affecting the design of the filter.

In the overall microfiltration operational model, blood flow through the expanded channel section of the microfilter devices was modeled using the device layout and parameters shown in FIG. 28. In the hydrodynamic model, the total pressure drop over the device was assumed to be constant, and it was estimated from the apparent capillary pressure in the expanded channel. Using the viscosity assumptions stated above, the average velocities in the expanded and filtration channels were calculated in an iterative manner until the relationships shown in equations (17-20) were satisfied. These relationships are based on a constant total pressure drop, and satisfying continuity requirements.

$$Q_n = Q_e \quad (17)$$

$$P_{cap} = \Delta P_n + \Delta P_e \quad (18)$$

$$\Delta P_e = \frac{3 u_e L_e \mu_e}{k_{e2-d} h^2} \quad (19)$$

$$\Delta P_n = \frac{3 u_n L_n \mu_n}{k_{n2-d} h^2} \quad (20)$$

Once the expanded channel velocity was calculated using the flow model described above, it was then used to predict the advancement of blood in the expanded channel at one-second time intervals per equation (21) to determine values of $L_e$ over time. Using the new value of $L_e$, the expanded and narrow filtration velocities are again calculated in an iterative manner as describe above. The model calculations proceed in this iterative fashion until the wall shear rate in the expanded channel reaches the minimum level of <75 s$^{-1}$. This design constraint determines the end-point for flow in the expanded channel, thus defining the total time of operation and total length of the expanded channel. The overall result of this quasi steady state flow model is an estimate of velocity in the expanded and filtration channels over the operating time of the device.

$$L_e(t+1)=L_e(t)+V_e(t) \quad (21)$$

Once the blood velocity in the expanded channel is determined, it is used to calculate the time-averaged wall shear rate in the filtration channel. Plasma flux is then predicted using the empirical wall shear rate model previously discussed in Chapter 6, equation (16). Total plasma volume extracted can then be calculated based on the plasma flux, time of operation, and filter area. Additionally, the average change in blood hematocrit due to fractionation of plasma was estimated. This result is used to verify compliance to the design rule specifying a maximum allowable change in hematocrit of $\leq 10\%$.

Figure 29:
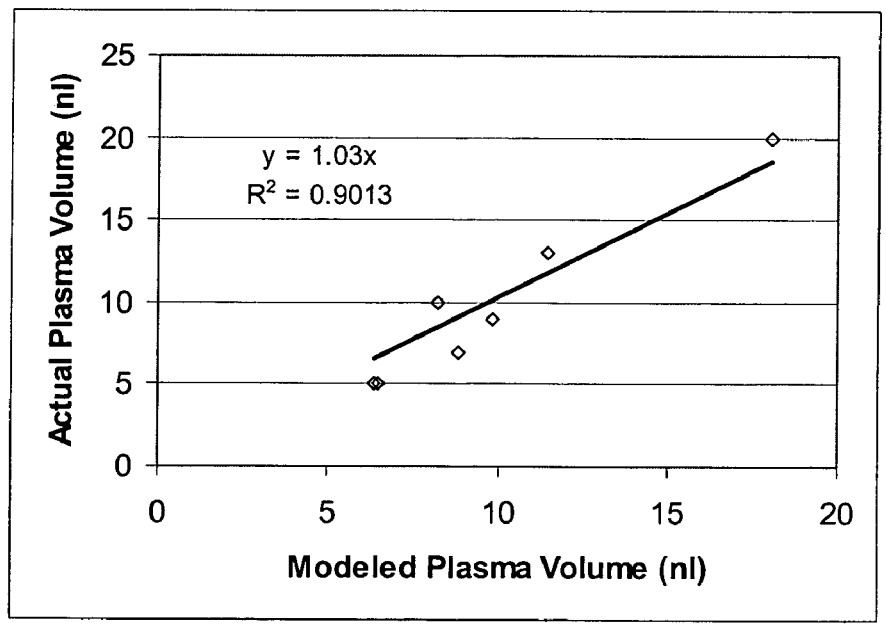
FIG. 29 is a plot of actual plasma volume vs. modeled plasma volume for a microfilter in accordance with the present invention.

As part of the model development and validation, the experimental results obtained from Weir 11 devices, which met the design rule for maximum allowable change in hematocrit, were compared to the operational model predictions. FIG. 29 shows the model results for plasma volume fractionated versus the experimentally observed values. As can be seen, the model predictions are in good agreement with the experimental results.

The operational model can be utilized to calculate microfilter device performance over a wide range of device dimensions, which can be used to determine optimum designs. The key device dimensions include filtration channel length, channel height, and total width of the expanded channel. An example of the operational model output is shown in the response surface plot of FIG. 30. This plot shows the predicted relationship between total fractionated plasma volume, filtration channel length and expanded channel width. Using the resulting color model to visualize and compare various combinations of design parameters indicates that there are combinations of expanded channel dimensions and filtration channel lengths where optimum device performance is attainable. In this case, the maximum volume of plasma fractionated determines the optimum performance criteria.

Figure 30:
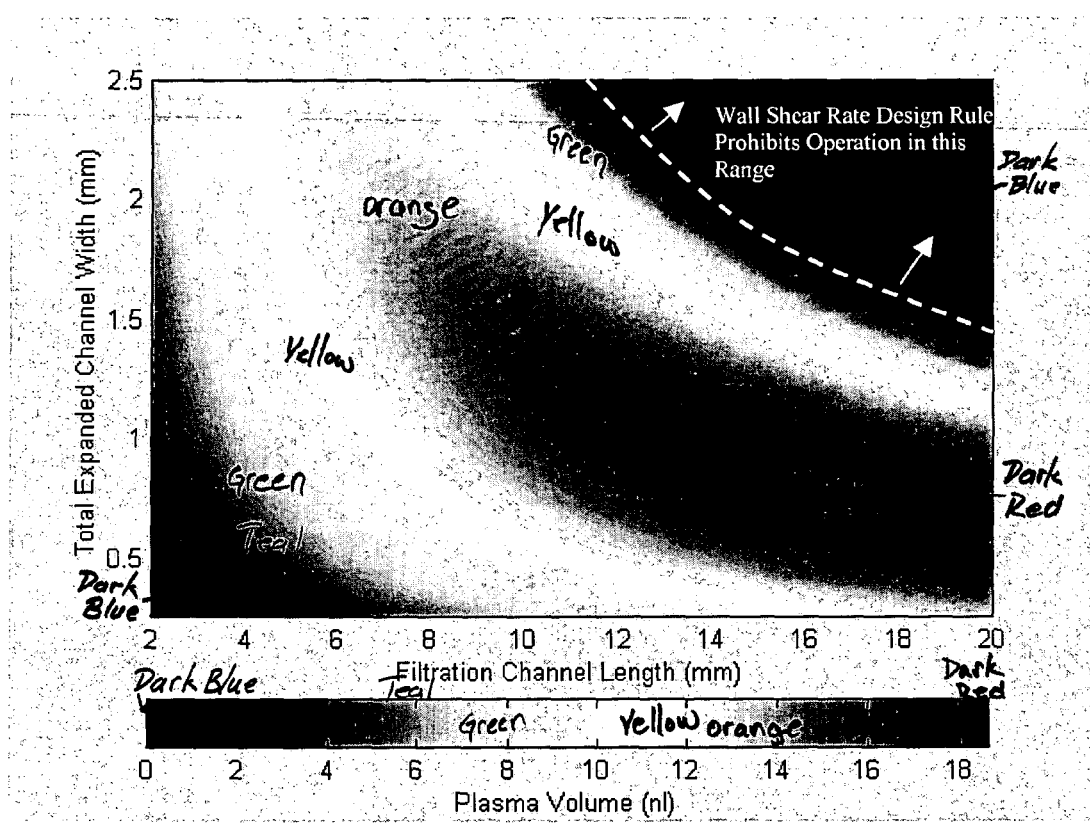
FIG. 30 is a plot of expanded channel width vs. filtration channel length with shadings indicating plasma volume from a microfilter in accordance with the invention.
Figure 31A:
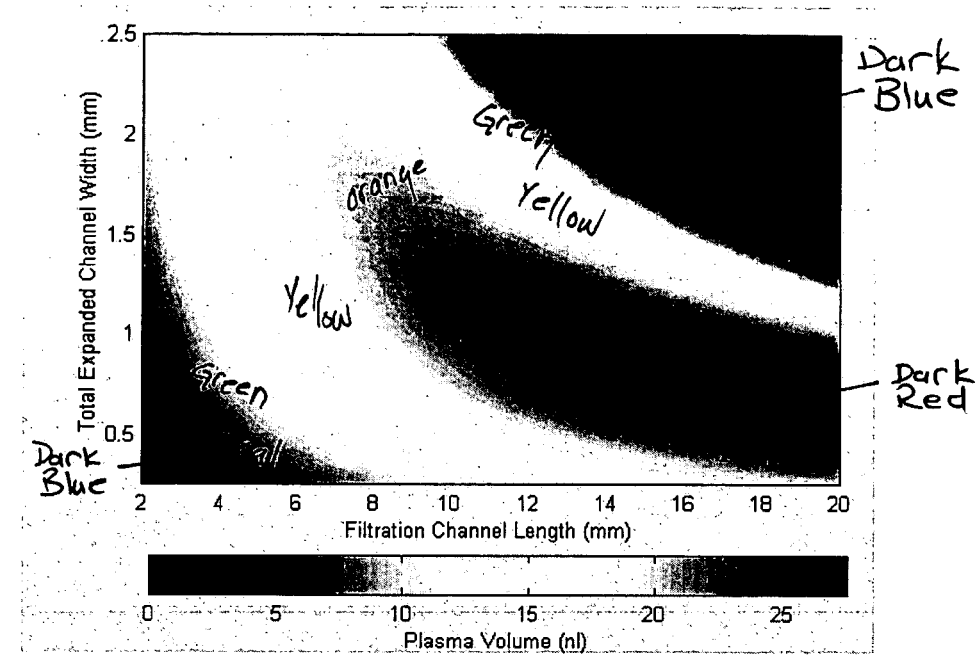
FIGS. 31a and b are plots of expanded channel width vs. viltration channel length first without (a) and then with (b) limitations imposed by wall sheer rate limit and hematocrit design rule limitation.
Figure 31B:
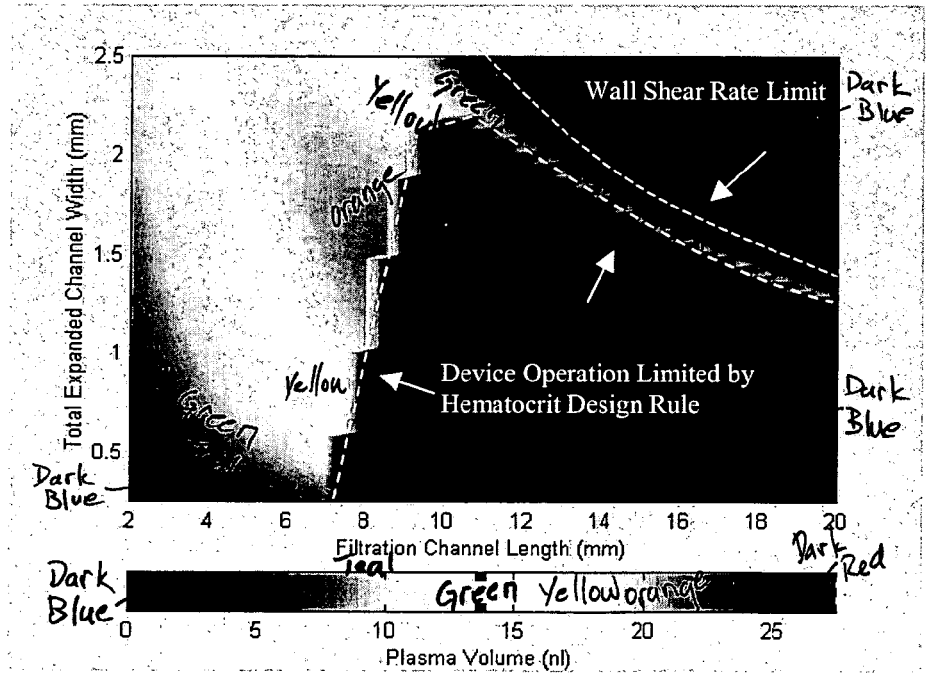

When the operational model is applied over a wide range of device dimensions, a portion of the evaluated design space typically will not satisfy the design rule requirements for the minimum expanded channel wall shear rate or maximum change in hematocrit or both. If these constraints are not met, the operation model assigns a zero value for the plasma volume isolated. For example, the upper right orner of FIG. 30 shows the portions of the design space that did not meet the minimum shear rate requirement, and this area was assigned a zero plasma volume value. In a second example of operational modeling (FIGS. 31a & b), the effect of both the hematocrit and minimum wall shear rate design rules on the usable design space can be seen. The top panel of FIGS. 31a & b shows an operational model that is unconstrained by the hematocrit design rule, and the bottom panels shows the reduction in available design space when the hematocrit design rule is applied. The hematocrit design rule significantly reduces the usable design space, and prohibits the attainment of the optimal design condition. Recall that the hematocrit design rule was implemented to avoid a large increase in apparent expanded channel viscosity and associated blood instability. In part this constraint is due to the formation of a blood cell plug at the leading edge of the flow, and this example, once again, illustrates how this phenomenon negatively impacts device design and optimization.

Although preferred embodiments of the invention have been described in detail, it will be readily appreciated by those skilled in the art that further modifications, alterations and additions to the invention embodiments disclosed may be made without departure from the spirit and scope of the invention as set forth in the appended claims.

We claim:

1. An instrument for observation, treatment, or analysis of a sample of a liquid comprising:
   a liquid input opening for receiving a liquid sample,
   a first passage leading from said liquid input opening to an expanded liquid flow region,
   at least one weir filter located tangentially along each side of said first passage between said liquid input opening and said expanded liquid flow region,
   at least one filtrate channel located on each side of said first passage parallel to said first passage,
   said at least one weir filter in communication with said first passage and said at least one filtrate channel located on the same side of said first passage as said at least one weir filter, and
   said liquid flow expanded region comprising a plurality of parallel capillary channels sized to sustain a draw of said liquid sample through said first passage tangentially past said at least one weir filter by capillary action.

2. The instrument according to claim 1, wherein said liquid sample is a complex fluid.

3. The instrument according to claim 1, wherein said draw of said liquid sample through said first passage tangentially past said at least one weir filter by capillary action filters said liquid sample into at least one filtrate flow in said at least one filtrate channel and a remaining liquid sample flow in said first passage.

4. The instrument according to claim 1, wherein said plurality of parallel capillary channels are sized to sustain a draw of said liquid sample through said first passage for a predetermined amount of time.

5. The instrument according to claim 3, wherein said plurality of parallel capillary channels are sized to produce at least a nanoliter of said at least one filtrate flow from said at least one filter.

6. The instrument according to claim 3, wherein said at least one filtrate channel further comprises a testing location in which at least a portion of said at least one filtrate flow is collected for analysis.

7. The instrument according to claim 6, wherein the analysis of said at least one filtrate flow includes electro-optical analysis.

8. The instrument according to claim 7, wherein said electro-optical analysis comprises a laser, a first reflective sidewall at said testing location positioned to direct laser light from the laser through said test location, a photodetector, and a second reflective sidewall at said testing location positioned to direct laser light from said test location to the photodetector.

9. The instrument according to claim 2, wherein said complex fluid is a biological fluid.

10. The instrument according to claim 9, wherein said biological fluid comprises at least one formed element.

11. The instrument according to claim 10, wherein said at least one weir filter lyses at least a portion of said at least one formed element.

12. The instrument according to claim 10, wherein said plurality of parallel capillary channels are sized to control the degree of lysing of said at least one formed element.

13. The instrument according to claim 1, wherein each capillary channel of said plurality of parallel capillary channels are about 45 µm wide and at least 10 µm in length.

14. The instrument according to claim 1, wherein said at least one weir filter comprises a channel having width of about 200 µm along the side of said first passage, a height of about 1 µn, and a length of about 30 µm coupling said first passage to said filtrate channel.

15. The instrument according to claim 6, wherein said analysis comprises at least one of an identification of at least one analyte in said at least one filtrate flow, a quantification of the concentration of at least one analyte in said at least one filtrate flow, and an isolation of at least one analyte in said at least one filtrate flow.

16. The instrument according to claim 15, wherein said at least one analyte in said at least one filtrate flow comprises at least one of a protein, an amino acid, an enzyme, an electrolyte, a nucleotide, and a dissolved gasses.

17. The instrument according to claim 1, wherein said expanded liquid flow region comprises a total width from about 0.4 to 2.5 mm and a length of from about 2 to 20 mm.

18. The instrument according to claim 1, wherein said a plurality of parallel capillary channels have a cross-sectional dimension a, where 0.3 µm>a>0.1 µn.

19. The instrument according to claim 3, wherein said at least one filtrate flow comprises a plasma filtrate.

* * * * *